(12) United States Patent
da Costa Garcia et al.

(10) Patent No.: US 8,563,504 B2
(45) Date of Patent: Oct. 22, 2013

(54) ANTIBACTERIAL PHAGE PEPTIDES AND METHODS OF USE THEREOF

(75) Inventors: Miguel Ângelo da Costa Garcia, Lisbon (PT); Madalena Maria Vilela Pimentel, Lisbon (PT); Carlos Jorge Sousa de São José, Lisbon (PT)

(73) Assignee: Lusomedicamenta, S.A., Barcarena (PT)

( * ) Notice: Subject to any disclaimer, the term of this patent is extended or adjusted under 35 U.S.C. 154(b) by 0 days.

(21) Appl. No.: 13/122,190

(22) PCT Filed: Oct. 9, 2009

(86) PCT No.: PCT/PT2009/000051
§ 371 (c)(1),
(2), (4) Date: Jun. 7, 2011

(87) PCT Pub. No.: WO2010/041970
PCT Pub. Date: Apr. 15, 2010

(65) Prior Publication Data
US 2011/0230393 A1    Sep. 22, 2011

Related U.S. Application Data

(60) Provisional application No. 61/104,594, filed on Oct. 10, 2008.

(51) Int. Cl.
*A01N 37/18* (2006.01)

(52) U.S. Cl.
USPC ............... 514/2.7; 514/1.1; 514/2.3; 514/2.4; 514/21.2; 530/350

(58) Field of Classification Search
None
See application file for complete search history.

(56) References Cited

U.S. PATENT DOCUMENTS 5,428,016 A * 6/1995 Tomita et al. ............... 514/2.3

FOREIGN PATENT DOCUMENTS

WO    WO 2004/020635    3/2004

OTHER PUBLICATIONS

Zou D. et al, "Prophage, PV83-pro, carrying panton-valentine leukocidin genes, on the *Staphylococcus aureus* P83 chromosome: Comparative analysis of the genome structures of PV83-pro, PVL, 11, and other phages." Biosci. Biotechnol. Biochem (2000) 64(12) p. 2631-2643.*

Havarstein L. S.; "An unmodified heptadecapeptide pheromone induces competence for genetic transformation in *Streptococcus pneumoniae*." Proc. Natl. Acad. Sci. USA, (1995) 92 p. 11140-11144.*

Strom M. B. et al; "The pharmacophore of short cationic antibacterial peptides." J. Med. Chem. (2003) 46(9) p. 1567-1570.*

Ruoslahti, E.; "RGD and other recognition sequences for integrins." Annu. Rev. Cell Dev. Biol. (1996) 12 p. 679-715.*

Song J. et al; "Molecular cloning and characterization of the cDNA coding for the biotin containing subunit of 3-methylcrotonoyl-CoA carboxylase: Identification of the biotin carboxylase and biotin carrier domains." Proc. Natl. Acad. Sci. USA. (1994) 91 p. 5779-5783.*

Database WPI Week 200422, Thomson Scientific, AN 2004-239200, Mar. 11, 2004.

Donovan et al., "LambdaSa2 Prophage Endolysin Requires Cpl-7-Binding Domains and Amidase-5 Domain for Antimicrobial Lysis of Streptorocci," FEMS Microbiology Letters, 287(1), pp. 22-33, Oct. 2008.

Horgan et al., "Phage Lysin LysK Can Be Truncated to Its CHAP Domain and Retain Lytic Activity against Live Antibiotic-Resistant Staphylococci," Applied and Environmental Microbiology, 755(3), pp. 872-874, Feb. 2009.

O'Flaherty et al., "The Recombinant Phage Lysin Lysk Has a Broad Spectrum of Lytic Activity Against Clinically Relevant Staphylococci, Including Methicillin-Resistant *Staphylococcus aureus*," Journal of Bacteriology, 187(20), pp. 7161-7164, Oct. 1, 2005.

Matsuzaki, et al., "*Staphylococcus aureus* related bacteriophage protein 9," Jun. 17, 2004, retrieved from http://www.ebi.ac.uk/Tools/es/cgi—bin/epo/epofetch.cgi?ADN01960>.

Rashel et al., "Efficient Elimination of Multidrug-Resistant *Staphylococcus aureus* by Cloned Lysin Derived from Bacteriophage ØMR11" Journal of Infectious Diseases, 196(8), pp. 1237-1247, Oct. 2007.

* cited by examiner

*Primary Examiner* — Cecilia J Tsang
*Assistant Examiner* — Fred Reynolds
(74) *Attorney, Agent, or Firm* — Margaret B. Brivanlou; Nicole Fortuné; King & Spalding LLP

(57) ABSTRACT

The present invention is directed to isolated and chimeric polypeptides of bacteriophage origin having antibiotic activity and use thereof in the treatment and control of bacterial infections. Specifically, the present invention is directed to the use of a novel antibacterial polypeptide derived from bacteriophage F87s/06 and chimeric constructs thereof, and their use for the treatment and control of infections caused by gram-positive bacteria, including *Staphylococcus aureus*.

2 Claims, 13 Drawing Sheets

```
P68    ------------MKSQQQAKEWIYKHEGAGVDFDGAYGFQCMDLSVAYVYYITDGKVRMW
Φ11    MSIIMEVATMQAKLTKNEFIEWLKTSEGKQFNVDLWYGFQCFDYANAGWKVLFGLLLKGL
Twort  ------------MKTLKQAESYIKSKVNTGTDFDGLYGYQCMDLAVDYIYHVTDGKIRMW
Lys87  ------------MKTYSEARARLRWYQGRYIDFDGWYGYDCADLAVDYIYWLLE--IRMW P68    GNAKDAINN-DFKGLATVYKNTPSFKPQLGDYAVYTN-----GQYSHIQCVLS----GN
Φ11    G-AKDIPFANNFDGLATVYQNTPDFLAQPGDMVVTGSNYG--AGYSHVAWVIE----AT
Twort  GNAKDAINN-SFGGTATVYKNTPAFRPKYGDYVVWTTGNF--ATYSHIALVTNPDPYGD
Lys87  GNAKDAINN-DFKNMATVYENTPSFVPQIGDYAVITKGIY--KQYSHIGLVTNG---GN P68    LDYYTCLEQNWLGGGFD        114
Φ11    LDYIIVYEQNWLGGGWT        129
Twort  LQYVTVLEQNWNGNGIY        121
Lys87  TNQFLILEQNYDGNANT        116
```

Figure 1 a)  ATGAAAACATACAGTGAAGCAAGAGCAAGGTTACGTTGGTATCAAGGTAGATATATTGA
TTTTGACGGTTGGTATGGTTACCAATGTGCAGATTTAGCAGTTGATTACATTTATTGGT
TGTTAGAAATTAGAATGTGGGGAAATGCAAAAGATGCAATCAATAACGATTTTAAAAAC
ATGGCAACAGTATATGAAAACACACCATCGTTTGTTCCACAAATAGGTGATGTGGCTGT
ATTTACCAAAGGAATATATAAACAATACGGTCATATTGGTTTAGTGTTTAATGGTGGTA
ATACAAACCAATTTTTAATTTTGGAACAGAACTATGACGGTAACGCAAATACGCCTGCA
AAGTTACGTTGGGATAATTATTACGGCTGTACTCACTTTATTAGACCTAAGTATAAAAG
TGAGGGCTTAATGAATAAGATCACAAATAAAGTTAAACCACCTGCTCAAAAAGCAGTCG
GTAAATCTGCAAGTAAAATAACAGTTGGAAGTAAAGCGCCTTATAACCTTAAATGGTCA
AAAGGTGCTTATTTTAATGCGAAAATCGACGGCTTAGGTGCTACTTCAGCCACTAGATA
CGGTGATAATCGTACTAACTATAGATTCGATGTTGGACAGGCTGTATACGCGCCTGGAA
CATTAATATATGTGTTTGAAATTATAGATGGTTGGTGTCGCATTTATTGGAACAATCAT
AATGAGTGGATATGGCATGAGAGATTGATTGTGAAAGAAGTGTTTTAA

SEQ ID NO: 1 b)  M K T Y S E A R A R L R W Y Q G R Y I D F D G W Y G Y
Q C A D L A V D Y I Y W L L E I R M W G N A K D A I N
N D F K N M A T V Y E N T P S F V P Q I G D V A V F T
K G I Y K Q Y G H I G L V F N G G N T N Q F L I L E Q
N Y D G N A N T P A K L R W D N Y Y G C T H F I R P K
Y K S E G L M N K I T N K V K P P A Q K A V G K S A S
K I T V G S K A P Y N L K W S K G A Y F N A K I D G L
G A T S A T R Y G D N R T N Y R F D V G Q A V Y A P G
T L I Y V F E I I D G W C R I Y W N N H N E W I W H E
R L I V K E V F

SEQ ID NO: 2

Figure 8 a)

ATGGCAGGAGAAGTATTTAGTAGCTTGATTACAAGTGTAAATCCTAACCCAATGAACGCAGGTAGCCGTAATGGTAT
CACTATCGACACCATTATCCTACATCACAATGCAACAACAAATAAAGATGTTGCTATGAACACATGGCTATTAGGTG
GTGGCGCAGGTACATCTGCTCATTATGAATGTACACCAACAGAAATTATTGGATGTGTCGGTGAGCAGTATTCAGCA
TTCCATGCCGGAGGTACAGGTGGTATAGACGTTCCTAAGATTGCTAACCCTAATCAACGTTCAATAGGTATTGAAAA
TGTAAACTCGTCAGGAGCACCTAATTGGTCTGTAGACCCTAGAACAATTACAAATTGTGCTCGTTTAGTGGCAGATA
TTTGTACACGTTATGGTATTCCGTGTGACCGACAACATGTGTTAGGACATAACGAAGTAACTGCAACAGCATGTCCC
GGAGGTATGGATGTAGACGAAGTTGTACGTCAAGCTCAACAGTTCATGGCAGGAGGCTCTAACAATGCAGTTAAGCC
GGAGCCAAAAGTTAAACCACCTGCTCAAAAAGCAGTCGGTAAATCTGCAAGTAAAATAACAGTTGGAAGTAAAGCGC
CTTATAACCTTAAATGGTCAAAAGGTGCTTATTTTAATGCGAAAATCGACGGCTTAGGTGCTACTTCAGCCACTAGA
TACGGTGATAATCGTACTAACTATAGATTCGATGTTGGACAGGCTGTATACGCGCCTGGAACATTAATATATGTGTT
TGAAATTATAGATGGTTGGTGTCGCATTTATTGGAACAATCATAATGAGTGGATATGGCATGAGAGATTGATTGTGA
AAGAAGTGTTT*CCCGGGGGGGGTTCTCATCATCATCATCATCATTAA*

SEQ ID NO:3 b)

MAGEVFSSLITSVNPNPMNAGSRNGITIDTIILHHNATTNKDVAMNTWLLGGGAGTSAHYECTPTEIIGCVGEQYSA
FHAGGTGGIDVPKIANPNQRSIGIENVNSSGAPNWSVDPRTITNCARLVADICTRYGIPCDRQHVLGHNEVTATACP
GGMDVDEVVRQAQQFMAGGSNNAVKPEPKVKPPAQKAVGKSASKITVGSKAPYNLKWSKGAYFNAKIDGLGATSATR
YGDNRTNYRFDVGQAVYAPGTLIYVFEIIDGWCRIYWNNHNEWIWHERLIVKEVF*PGGGSHHHHHH*

SEQ ID NO:4

Figure 9 a)

ATGGTTAAATTAAATGATGTACTTAGCTATGTCAACGGACTTGTCGGAAAAGGCGTGGACGCTGATGGATGGTATGG
TACTCAATGTATGGACTTGACAGTAGACGTTATGCAACGCTTCTTCGGATGGCGCCCGTACGGTAATGCAATTGCCT
TGGTTGACCAGCCTATCCCAGCAGGCTTCCAAAGAATCCGTACCACAAGCTCTACACAAATCAAAGCTGGTGACGTT
ATGATATGGGGCTTAGGATACTATGCTCAATACGGTCACACAGGAATTGCAACGGAGGATGGAAGAGCTGACGGAAC
CTTTGTCAGTGTTGACCAAAACTGGATTAACCCAAGCCTTGAAGTAGGCAGTCCAGCAGCTGCTATCCACCACAATA
TGGATGGTGTCTGGGGAGTTATCCGACCACCTTACGAGGCTGAATCAAAGCCTAAACCACCTGCACCAAAACCAGAT
AAACCAAATCTAGGACAAAAAGTTAAACCACCTGCTCAAAAAGCAGTCGGTAAATCTGCAAGTAAAATAACAGTTGG
AAGTAAAGCGCCTTATAACCTTAAATGGTCAAAAGGTGCTTATTTTAATGCGAAAATCGACGGCTTAGGTGCTACTT
CAGCCACTAGATACGGTGATAATCGTACTAACTATAGATTCGATGTTGGACAGGCTGTATACGCGCCTGGAACATTA
ATATATGTGTTTGAAATTATAGATGGTTGGTGTCGCATTTATTGGAACAATCATAATGAGTGGATATGGCATGAGAG
ATTGATTGTGAAAGAAGTGTTT*CCCGGGGGGGGTTCTCATCATCATCATCATCATTAA*

SEQ ID NO:5 b)

MVKLNDVLSYVNGLVGKGVDADGWYGTQCMDLTVDVMQRFFGWRPYGNAIALVDQPIPAGFQRIRTTSSTQIKAGDV
MIWGLGYYAQYGHTGIATEDGRADGTFVSVDQNWINPSLEVGSPAAAIHHNMDGVWGVIRPPYEAESKPKPPAPKPD
KPNLGQKVKPPAQKAVGKSASKITVGSKAPYNLKWSKGAYFNAKIDGLGATSATRYGDNRTNYRFDVGQAVYAPGTL
IYVFEIIDGWCRIYWNNHNEWIWHERLIVKEVF*PGGGSHHHHHH*

SEQ ID NO:6

Figure 10

ANTIBACTERIAL PHAGE PEPTIDES AND METHODS OF USE THEREOF

REFERENCE TO RELATED APPLICATION

This application claims the benefit of U.S. Provisional Application No. 61/104,594, filed Oct. 10, 2008, which is incorporated herein by reference in its entirety.

FIELD OF THE INVENTION

The present invention is directed to isolated and chimeric polypeptides of bacteriophage origin having antibiotic activity and use thereof in the treatment and control of bacterial infections. Specifically, the present invention is directed to the use of a novel antibacterial polypeptide derived from bacteriophage F87s/06 and chimeric constructs thereof, and their use for the treatment and control of infections caused by gram-positive bacteria, including *Staphylococcus aureus*.

BACKGROUND OF THE INVENTION

Bacteriophage (phage) are viruses that specifically infect and lyse bacteria. Phage therapy, a method of using whole phage viruses for the treatment of bacterial infectious diseases, was introduce by Felix d'Herelle, who discovered phage around 1920. In the beginning of the 20th century, there were various studies of the application of phage for therapy in humans as well as in animals. In 1940 Eli Lilly Company produced 7 phage products for human use, including phage preparations for treating different sicknesses caused by *Staphylococcus* sp., *E. coli* and other pathogenic bacteria. These preparations were utilized to treat infections that cause abscesses, purulent wounds, vaginitis, acute chronic upper-respiratory tract infections and mastoid infections.

However, with the arrival of antibiotics in the 1940's, the development of phage based therapeutics declined in the Western word. One of the most important factors that contributed to the decline of interest in phage therapy in the Western world was the problem of credibility. The reduction in the number of appropriately conducted studies and the lack of well-established protocols and standardizations interfered with the rigorous documentation of the value of phage therapy. Many problems related to the production of phage samples/specimens also complicated the initial study/research related to phage therapy. Diverse stabilizers and preservatives were used in attempts to increase the viability of the phage therapeutics. However, without a good understanding of the biological nature of phage and their stability in response to various physical and chemical agents, many of the ingredients added to prolong the viability of the phage preparations resulted in a negative effect on the viability of the phage, and in some cases proved to be toxic to humans. Another problem related to phage production was the purity grade of the commercial preparations of these viruses. The phage therapy preparations, including those originating from well-established companies in the United States and other countries, consisted of raw lysates of the host bacteria treated with the phage of interest. Thus, the preparations had bacterial components, including endotoxins, that could have adverse effects in patients treated with these preparations, particularly those receiving intravenous administration. However, the use of bacteriophage for therapeutic ends continued jointly with, or in place of antibiotics, in Eastern Europe and in the former Soviet Union where access to antibiotics was limited.

With the rise of antibiotic resistant strains of bacteria, interest in phage based therapeutics has gained broader interest. Even though novel classes of antibiotics may be developed, the prospect that bacteria will eventually develop resistance to the new drugs has intensified the search for non-chemotherapeutic means for controlling and treating bacterial infections. There are three general strategies for using phage-based therapies in a clinical environment: 1) the use of active, virulent phage; 2) the use of endolysins or purified lysins isolated from bacteriophage; and 3) the use of a structural protein of the identified phage as a metabolic inhibitor of key enzymes for the synthesis of bacterial peptidoglycan.

Among the most promising of the strategies currently in development are phage lysins. Preparations of purified endolysins can be used as therapeutic agents, per se, or combined with classic antibiotics. The addition of exogenous lysins to susceptible gram-positive bacteria can cause a complete lysis in the absence of bacteriophage (Loeffler et al., 2001, *Science* 294:2170-2172; Shuch et al., 2002, *Nature* 418:884-889). Microscopic images of bacteria treated with a lysin indicate that these enzymes exercise their lethal effect by digesting peptidoglycan leading to the formation of holes in the cell wall. Compared with the external environment, the inside of a bacterium is hypertonic, and when the bacterial wall loses its structural integrity the result is the extrusion of the cytoplasmic membrane and hypertonic lysis.

While penicillin and antibiotics of the Cephalosporin class inhibit the synthesis of peptidoglycan causing lysis of the bacterial cell wall during cell division, the phage lysins destroy the peptidoglycan directly, exercising their lytic effect seconds after being administered. The lysins can also destroy the cell wall of bacteria that are not growing and are insensitive to many antibiotics. When simultaneously administered, two lysins that have differing target sequences may attack the peptidoglycan in multiple regions, presenting a synergistic effect.

There is a clear need for further investigation of lysin enzymes as potential therapeutic and prophylactic agents of use, in vivo, to eliminate pathogenic bacteria without affecting the normal surrounding flora. Due to serious problems of resistant bacteria in hospitals, particularly *Staphylococcus* and *Pneumococcus* sp., these enzymes can be an immediate benefit in these types of environments.

However, most lysins discovered to date are specific to species (or subspecies) of bacteria from which they are produced. For example, it has been shown that lysins isolated from streptococcal phage only kill certain streptococci and that lysins produced by pneumococcal phage only kill pneumococci (Fishcetti, 2005, *Trends in Microbio* 13:491-496). Therefore, there is an increasing need to discover new and novel lysin enzymes that may be used to treat the increasing number of bacterial species that have developed antibiotic resistance. There is also a need to develop lysin constructs that permit species cross-reactivity. In particular, the isolation and/or development of novel lysins with lytic killing or antibacterial activity beyond the specific species from which they are isolated would be especially valuable.

SUMMARY OF THE INVENTION

The present invention is directed to isolated antibiotic polypeptides of bacteriophage origin, in particular, polypeptides from bacteriophage F87s/06 (infectious phage of *S. aureus*), as well as to chimeric constructs thereof. The isolated and chimeric polypeptides may be used in pharmaceutical compositions for the treatment or management of conditions associated with infection by Gram-positive bacteria, e.g., *Staphylococcus epidermidis, S. auricularis, S. capitis, S. haemolyticus, S. hominis, S. saprophyticus, S. siniulans, S. xylosis, Micrococcus luteus, Bacilus subtilis, B. pumilus, Enterococcus faecalis, E. hirae, E. faecium* and *E. avium*. In certain embodiments, the pharmaceutical compositions of the invention are of use in the treatment of conditions associated with infection by methicillin resistant strains of *Staphylococcus aureus* (MRSA).

In certain embodiments, the present invention is directed to polypeptides isolated from bacteriophage 87 (F87s/06), which polypeptides exhibit antibiotic and/or targeting activity against a Gram-positive bacterium, e.g., *S. aureus*. In specific embodiments, the polypeptide of the invention comprises or consists of the amino acid sequence SEQ ID NO:2. In other embodiments, a polypeptide of the invention comprises a fragment, variant or derivative of SEQ ID NO:2, wherein said fragment, variant or derivative has antibiotic (e.g., lytic killing activity) activity and/or targeting activity against a Gram-positive bacteria, e.g., *S. aureus*. In a specific example in accordance with this embodiment, the invention provides for polypeptides having an amino acid sequence with at least 60%, 65%, 70%, 75%, 85%, 95%, 90%, 95%, 96%, 97%, 98%, 99%, or greater sequence identity to a second amino acid sequence of the same length (i.e., consisting of the same number of residues), wherein the second amino acid sequence is SEQ ID NO: 2, or a fragment thereof.

In certain embodiments, the present invention is directed to chimeric polypeptides derived from bacteriophage 87 (F87s/06), which chimeric polypeptides exhibit antibiotic activity against a Gram-positive bacterium, e.g., *S. aureus*. The chimeric polypeptide may be derived from an isolated polypeptide of the invention where a catalytic domain of the isolated polypeptide is substituted with a catalytic domain of a heterologous lysin protein, such as a heterologous lysin protein from phage F170/08 or phage F168/08 that has antimicrobial or antibiotic activity against *S. aureus*. In specific embodiments, the chimeric polypeptide comprises or consists of the amino acid sequence SEQ ID NO:4 or SEQ ID NO:6, or a fragment of either having antimicrobial. or antibiotic activity against *S. aureus*. In other embodiments, the chimeric polypeptide comprises a fragment, variant or derivative of SEQ ID NO:4 or 6, wherein the fragment, variant or derivative has antibiotic activity or antimicrobial activity (e.g., lytic killing activity) against a Gram-positive bacteria, e.g., *S. aureus*. In a specific example in accordance with this embodiment, the invention provides for chimeric polypeptides having an amino acid sequence with at least 60%, 65%, 70%, 75%, 85%, 95%, 90%, 95%, 96%, 97%, 98%, 99%, or greater sequence identity to an amino acid sequence of the same length (i.e., consisting of the same number of residues) and having amino acid sequence SEQ ID NO: 4 or 6, or a fragment of either.

The invention also encompasses polynucleotides that encode the polypeptides of the invention. In a specific embodiment, the invention provides an isolated nucleic acid comprising a nucleic acid sequence encoding a polypeptide of F87s/06, or active fragment thereof, which polypeptide or fragment exhibits antibiotic activity (e.g., lytic killing activity) and/or targeting activity against a Gram-positive bacteria, e.g., *S. aureus*. In a specific example in accordance with this embodiment, the invention provides for a nucleic acid comprising or consisting of the nucleic acid sequence SEQ ID NO:1, or a fragment thereof. The invention also relates to a vector comprising said nucleic acid. In one specific embodiment, said vector is an expression vector. The invention further provides host cells containing a vector comprising polynucleotides encoding the polypeptides of the invention.

In another specific embodiment, the invention provides an chimeric nucleic acid comprising a nucleic acid sequence encoding a polypeptide of phage F87s/06, or active fragment thereof, wherein a catalytic domain of the isolated polypeptide or active fragment is substituted with a catalytic domain of a heterologous lysin protein. In a specific example in accordance with this embodiment, the invention provides for a nucleic acid comprising or consisting of the nucleic acid sequence SEQ ID NO:3 or 5, or a fragment thereof. The invention also relates to a vector comprising said chimeric nucleic acid. In one specific embodiment, said vector is an expression vector. The invention further provides host cells containing a vector comprising polynucleotides encoding the chimeric polypeptides of the invention.

The invention encompasses methods for the evaluation of antibiotic activity of isolated and chimeric polypeptides (e.g., killing based on the antimicrobial activity and/or lytic activity of the polypeptides of the invention). Antibiotic activity may be assessed by any method known in the art and/or described herein. in certain embodiments, antibiotic activity is assessed by culturing Gram-positive bacteria according to standard techniques (e.g., in liquid culture or on agar plates), contacting the culture with polypeptides of the invention and monitoring cell growth after said contacting. For example, in a liquid culture, the bacteria, e.g., *S. aureus*, may be grown to an optical density ('OD') representative of a mid-point in exponential growth of the culture; portions of the culture exposed to one or more concentrations of one or more polypeptides of the invention and the OD monitored relative to a control culture. Decreased OD relative to a control culture is representative of a polypeptide exhibiting antibiotic activity (e.g., exhibits antimicrobial and/or lytic killing activity). Similarly, bacterial colonies can be allowed to form on an agar plate, the plate exposed to a polypeptide of the invention, and the subsequent growth of the colonies evaluated compared to control plates. Decreased size of colonies, or decreased total numbers of colonies indicate a polypeptide with antibiotic activity.

'Targeting activity' also may be assessed by any method known in the art and/or described herein. For example, targeting activity towards a particular bacterial host may be assessed by creating chimeric polypeptides comprising a candidate sequence and a catalytic domain from a lysin known to cause lysis of the particular host cells. In such an experiment, antibiotic activity of the chimeric molecule can be used as an indication of the targeting activity of the candidate sequence.

The present invention encompasses methods for the production of polypeptides of the invention or active fragments thereof, particularly for use in pharmaceutical compositions, e.g., antibiotic or antimicrobial compositions. In certain embodiments, the polypeptides of the invention are isolated directly from cell cultures (e.g. bacterial cell cultures) infected with bacteriophage F87s/06 using standard techniques known in the art and/or described herein. In other embodiments, the polypeptides of the present invention are produced by recombinant means using an expression vector comprising a nucleic acid sequence encoding a polypeptide of the invention, e.g., SEQ ID NO: 2, 4 or 6, or an active fragment, derivative or variant thereof (i.e., which active fragment has antibiotic and/or targeting activity).

The polypeptides of the invention or fragments thereof can be produced by any method known in the art for the production of a polypeptide, in particular, by chemical synthesis or by recombinant expression techniques. In a specific embodiment, the invention relates to a method for recombinantly producing a lysin protein of the invention, or active fragment thereof, said method comprising: (i) culturing under conditions suitable for the expression of said protein in a medium, a host cell containing a vector comprising the nucleic acid sequence SEQ ID NO:1 or fragment thereof; and (ii) recovery of said protein from said medium. In certain embodiments, the nucleic acid sequence encoding the polypeptide of the invention is operably linked to a heterologous promoter. 'Heterologous' as used herein refers to a combination of elements not naturally occurring.

In another specific embodiment, the invention relates to a method for recombinantly producing a chimeric polypeptide of the invention, or active fragment thereof, said method comprising (i) constructing a chimeric nucleic acid encoding a chimeric polypeptide of the instant invention; (ii) culturing in a medium a host cell comprising the chimeric nucleic acid, under conditions suitable for expressing the chimeric polypeptide; and (iii) recovering the chimeric polypeptide from the medium. In certain embodiments, the chimeric nucleic acid sequence encoding the chimeric polypeptide of the invention is operably linked to a heterologous promoter. In certain preferred embodiments, the chimeric nucleic acid comprises a sequence derived from a bacteriophage F87s/06 lysin protein and a sequence derived from a heterologous lysin protein, such as a sequence from bacteriophage F170/08 or F168/08 that has antibiotic or antimicrobial activity. The sequence derived from phage F87s/06 may comprise a targeting domain, while the sequence derived from phage F170/08 or F168/08 may comprise a catalytic domain that has antibiotic or antimicrobial activity against *S. aureus*, for example, when targeted thereto.

The present invention encompasses pharmaceutical compositions comprising polypeptides isolated or derived from bacteriophage F87s/06, in particular isolated or chimeric polypeptides having antimicrobial and/or antibiotic activity. The pharmaceutical compositions of the invention may additionally comprise a pharmaceutically acceptable carrier, excipient, or stabilizer. In specific embodiments, the pharmaceutical compositions comprise a polypeptide having the amino acid sequence of SEQ ID NO: 2. In another embodiment, the pharmaceutical compositions comprise a polypeptide that is a variant, derivative or fragment of SEQ ID NO: 2, wherein the variant, derivative or fragment retains antimicrobial and/or targeting activity against a Gram-positive bacteria, e.g., *S. aureus*. In other specific embodiments, the pharmaceutical compositions comprise a chimeric polypeptide having the amino acid sequence of SEQ ID NO: 4 or 6. In another embodiment, the pharmaceutical compositions comprise a chimeric polypeptide that is a variant, derivative or fragment of SEQ ID NO:4 or 6, wherein the variant, derivative or fragment retains antimicrobial and/or antibiotic activity against a Gram-positive bacteria, e.g., *S. aureus*.

In specific embodiments, the pharmaceutical compositions of the invention are antibiotic compositions or therapeutic compositions for the treatment, prevention, and/or amelioration of symptoms of a disease or disorder associated with infection by a Gram-positive bacteria in a subject in need thereof. The subject receiving a pharmaceutical composition of the invention may be a mammal (e.g., bovine, ovine, caprine, equid, primate (e.g., human), rodent, lagomorph) or avain (e.g., chicken, duck, goose). In the context of the present invention, 'treatment' refers to both therapeutic treatment and prophylactic or preventative measures, wherein the object is to eliminate, lessen, decrease the severity of, slow the progression of or prevent the symptoms or underlying cause (e.g., bacterial infection) associated with the pathological condition or disorder. The pharmaceutical compositions of the present invention may be used in the treatment or management of infections associated with any gram-positive bacteria, including, but not limited to *Staphylococcus aureus*, *S. epidermidis*, *S. auricularis*, *S. capitis*, *S. haemolyticus*, *S. hominis*, *S. saprophyticus*, *S. simulans*, *S. xylosis*, *Micrococcus luteus*, *Bacilus subtilis*, *B. pumilus*, *Enterococcus faecalis*, *E. hirae*, *E. faecium E. avium*, and combinations thereof. The pharmaceutical compositions may also be used to treat conditions or disorders associated with bacterial infections including, but not limited to, post-operative endophtalmitis, endocarditis, infections of the central nervous system, pneumonia, osteomylelitis, wound infections (e.g., diabetic foot ulcers), mastitis, septicemia, food poisoning and meningitis.

In certain embodiments, the invention provides for the use of lysin polypeptides as a single agent therapy. In another embodiment, the lysin polypeptides of the present invention may be combined with one or more lysins from a bacteriophage other than bacteriophage F87s/06, such as with lysins from bacteriophage F170/08 or F168/08, e.g., to produce chimeric polypeptides. In yet other embodiments, the invention provides for the use of a lysin polypeptide, or active fragment, variant, derivative, or chimeric construct thereof, in combination with a standard or experimental treatment for Gram-positive bacterial infection. In still other embodiments, the invention provides for the use of a lysin protein, chimeric construct, or active fragment of either, that has been chemically conjugated to still another therapeutic molecule (e.g., peptide or non-peptide cytotoxin). Such combination therapy may enhance the efficacy of the standard or experimental treatment. Examples of therapeutic agents that are particularly useful in combination with a polypeptide of the invention are anti-inflammatory agents, standard chemotherapeutic antibiotic agents (e.g., penicillin, synthetic penicillins, bacitracin, methicillin, cephalosporin, polymyxin, cefaclor. Cefadroxil, cefamandole nafate, cefazolin, cefixime, cefmetazole, cefonioid, cefoperazone, ceforanide, cefotanme, cefotaxime, cefotetan, cefoxitin, cefpodoxime, proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and chelating agents). The combination therapies encompassed by the invention may be formulated into a single pharmaceutical composition or may be administered in separate compositions as part of an overall treatment regimen.

The pharmaceutical compositions of the invention may be administered by any method known in the art suitable for administration of an antibiotic compound (e.g., via oral or parenteral (e.g., inhalation, intramuscular, intravenous, or epidermal delivery).

The pharmaceutical compositions of the present invention may also be used for traditionally non-therapeutic uses such as antibacterial agents in cosmetics, or in sprays or solutions for use on solid surfaces to prevent the colonization of Gram-positive bacteria (e.g., as a disinfectant or anti-infectant).

The present invention is also directed to methods for screening peptides for antibiotic and/or targeting activity. In one embodiment the method comprises screening contiguous amino acid sequences of at least 6, 10, 15, 20 or 25 residues in length from SEQ ID NO: 2, or 4, or 6 for antibiotic and/or targeting activity, said antibiotic and/or targeting activity measured by the peptide's ability to inhibit bacterial growth in agar or liquid culture.

BRIEF DESCRIPTION OF THE DRAWINGS

FIG. 1 shows an alignment of the N-terminal region of Lys87 with the endolysins of phage P8. Twort, and Φ11. The conserved residues known to be present in endopeptidase domains are indicated by boxes.

FIGS. 8a and 8b show the nucleic acid sequence (SEQ ID NO:1) and its encoded amino acid sequence (SEQ ID NO:2), respectively, of a lysin peptide isolated from bacteriophage F87s/06.

FIGS. 9a and 9b show the nucleic acid sequence (SEQ ID NO:3) and its encoded amino acid sequence (SEQ ID NO:4), respectively, of the chimeric construct lysin 170-87. Sequences deriving from gene lys170 are in bold; sequences from gene lys87 are in plain text; vector born sequences are in italics.

FIGS. 10a and 10b show the nucleic acid sequence (SEQ ID NO:5) and its encoded amino acid sequence (SEQ ID NO:6), respectively, of the chimeric construct lysin168-87. Sequences deriving from gene lys168 are in bold; sequences from gene lys87 are in plain text; vector born sequences are in italics.

DETAILED DESCRIPTION OF THE INVENTION

Definitions

Figure 2:
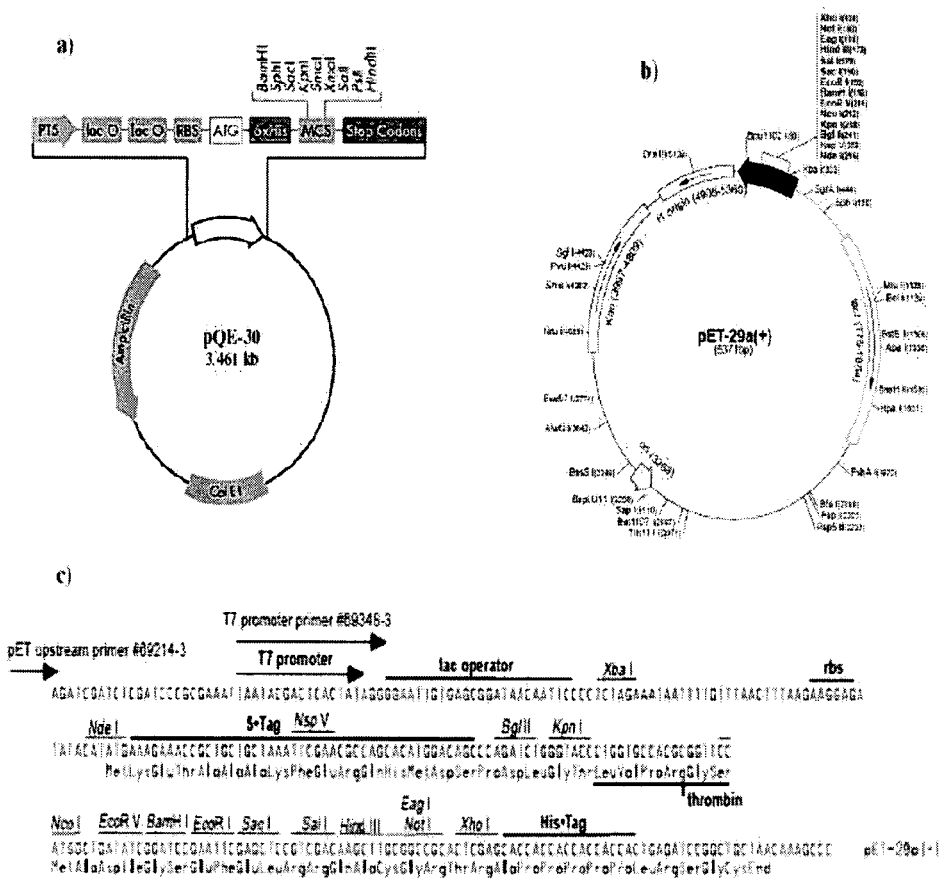
FIGS. 2a-2c are schematic representation of expression vectors pQE-30 (a) and pET-29 (b and c).

As used herein, the term 'fragment' refers to a peptide or polypeptide comprising an amino acid sequence of at least S contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, or at least contiguous 200 amino acid residues of the amino acid sequence of a second polypeptide. In a specific embodiment, the fragment is a functional fragment in that it retains at least one function of the second polypeptide (e.g., antimicrobial or antibiotic activity; or targeting activity).

As used herein, the term 'isolated' in the context of a peptide, polypeptide or fusion protein refers to a peptide, polypeptide or fusion protein that is substantially free of cellular material or contaminating proteins from the cell or tissue source from which it is derived, or substantially free of chemical precursors or other chemicals when chemically synthesized. The language 'substantially free of cellular material' includes preparations of a peptide, polypeptide or fusion protein in which the peptide, polypeptide or fusion protein is separated from cellular components of the cells from which it is isolated or recombinantly produced. Thus, a peptide, polypeptide or fusion protein that is substantially free of cellular material includes preparations of a peptide, polypeptide or fusion protein having less than about 30%, 20%, 10%, or 5% (by dry weight) of heterologous protein (also referred to herein as a 'contaminating protein'). When the peptide, polypeptide or fusion protein is recombinantly produced, it is also preferably substantially free of culture medium, i.e., culture medium represents less than about 20%, 10%, or 5% of the volume of the protein preparation. When the peptide, polypeptide or fusion protein is produced by chemical synthesis, it is preferably substantially free of chemical precursors or other chemicals, i.e., it is separated from chemical precursors or other chemicals which are involved in the synthesis of the peptide, polypeptide or fusion protein. Accordingly such preparations of a peptide, polypeptide or fusion protein have less than about 30%, 20%, 10%, 5% (by dry weight) of chemical precursors or compounds other than the peptide, polypeptide or fusion protein of interest.

As used herein, the term 'isolated' in the context of nucleic acid molecules refers to a first nucleic acid molecule which is separated from other nucleic acid molecules which are present in the natural source of the first nucleic acid molecule. Moreover, an 'isolated' nucleic acid molecule, such as a cDNA molecule, is substantially free of other cellular material, or culture medium when produced by recombinant techniques, or substantially free of chemical precursors or other chemicals when chemically synthesized and may be free of cDNA or other genomic DNA molecules, e.g., where it has been isolated from other clones in a nucleic acid library.

The term 'purified' means that the lysin or chimeric lysin construct has been measurably increased in concentration by any purification process, including but not limited to, column chromatography, HPLC, precipitation, electrophoresis, etc., thereby partially, substantially, or completely removing impurities such as precursors or other chemicals involved in preparing the lysin or chimeric lysin construct. One of ordinary skill in the art will appreciate the amount of purification necessary for a given use. For example, isolated protein meant for use in therapeutic compositions intended for administration to humans ordinarily must be of high purity in accordance with regulatory standards (e.g., of higher purity than isolated proteins for laboratory use).

As used herein, the term 'derivative' in the context of polypeptides refers to a polypeptide that comprises an amino acid sequence which has been altered by the introduction of amino acid residue substitutions, deletions or additions. The term 'derivative' as used herein also refers to a polypeptide that has been modified, i.e., by the covalent attachment of any type of molecule to the polypeptide. For example, but not by way of limitation, polypeptides may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide may contain one or more non-classical amino acids. A polypeptide derivative may possess a similar or identical function as the polypeptide from which it was derived, or it may possess an improved function. The term 'derived' as used in reference to a polypeptide 'derived' from an organism may also refer to isolation of a polypeptide directly from said organism (e.g. bacterial cells or phage).

As used herein, the term 'chimeric' refers to a construct derived from two or more heterologous sources. A chimeric gene or chimeric nucleic acid, for example, can comprise sequences derived from a first nucleic acid combined with sequences derived from a second nucleic acid, where the first and second nucleic acids are native to different types of bacteriophage. The sequences from each nucleic acid typically correspond to coding sequences for a functional domain of the respective encoded polypeptides. The heterologous nucleic acid sequences may be combined in frame, e.g., by recombinant means, so as to encode a fusion protein or chimeric polypeptide, which can be expressed thereform under appropriate conditions. A chimeric polypeptide can be engineered to include the full sequence of two or more native proteins, or only a portion of either. Chimeric polypeptides generally are created to impart functionality from each of the original proteins to the resulting chimeric polypeptides. The dual (or higher order) functionality of fusion proteins is made possible by the fact that protein functional domains are generally modular, such that a linear portion of a polypeptide constituting a given domain, such as catalytic domain, may be removed from the rest of the protein without destroying its enzymatic capability. A chimeric nucleic acid or chimeric polypeptide comprising sequences derived from two or more different lysin genes or polypeptides can be referred to as a 'chimeric lysin' or 'chimeric lysin construct'.

As used herein, the term 'host cell' refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term 'in combination' refers to the use of more than one prophylactic and/or therapeutic agent. The use of the term 'in combination' does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject with a disease or disorder.

As used herein, the terms 'nucleic acids' and 'nucleotide sequences' include DNA molecules (e.g., cDNA or genomic DNA), RNA molecules (e.g., mRNA), combinations of DNA and RNA molecules, chimeric DNA and RNA molecules, or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably are double-stranded DNA.

As used herein, the terms 'prophylactic agent' and 'prophylactic agents' refer to polypeptides of the invention, which can be used in the prevention, treatment, management or amelioration of one or more symptoms associated with infection by a Gram-positive bacteria.

As used herein, the terms 'therapeutic agent' and 'therapeutic agents' refer to polypeptides of the invention that can be used in the prevention, treatment, management or amelioration of one or more symptoms of a disease or disorder or of the underlying cause of the disease or disorder (e.g., infection by a bacteria).

As used herein, the term 'therapeutically effective amount' refers to that amount of a therapeutic agent sufficient to result in amelioration of one or more symptoms of a disease or disorder (e.g., a disease or disorder associated with infection by Gram-positive bacteria) in a subject or to result in a reduction in total bacterial burden in said subject.

As used herein, the terms 'treat', 'treatment' and 'treating' refer to the amelioration of one or more symptoms associated with an infection by Gram-positive bacteria or to the reduction in total bacterial burden that results from the administration of one or more polypeptides of the invention.

The term 'antibiotic activity' refers to the ability to kill and/or inhibit the growth or reproduction of a microorganism and can be used interchangeably with 'antimicrobial activity'. In certain embodiments, antibiotic or antimicrobial activity is assessed by culturing Gram-positive bacteria according to standard techniques (e.g., in liquid culture or on agar plates), contacting the culture with polypeptides of the invention and monitoring cell growth after said contacting. For example, in a liquid culture, the bacteria, e.g., *S. aureus*, may be grown to a optical density ('OD') representative of a mid-point in exponential growth of the culture; the culture exposed to one or more concentrations of one or more polypeptides of the invention and the OD monitored relative to a control culture. Decreased OD relative to a control culture is representative of a polypeptide exhibiting antibiotic activity (e.g., exhibits lytic killing activity). Similarly, bacterial colonies can be allowed to form on an agar plate, the plate exposed to a polypeptide of the invention, and subsequent growth of the colonies evaluated related to control plates.

Decreased size of colonies, or decreased total numbers of colonies indicate a polypeptide with antibiotic activity. A fragment, variant, or derivative of a lysin polypeptide having antibiotic or antimicrobial activity refers to the fragment having the catalytic ability to bring about host bacterial cell death, or to the fragment having such catalytic ability as well as targeting activity towards the host, as defined below.

The term 'targeting activity' refers to the ability of a lysin polypeptide to direct catalytic activity, such as antibiotic or antimicrobial activity, to a given bacterial host cell. Targeting activity may be associated with a particular region or domain of the polypeptide, such that, e.g., a chimeric construct comprising a targeting domain of a first lysin polypeptide, native to a first host species, can direct the catalytic activity, such as the antibiotic activity, of the chimeric construct to bacterial cells of first host species. As used herein, targeting activity 'towards' a particular host cell or bacterial species is used interchangeably with the related expressions targeting activity 'to' or 'against' the host cell or bacterial species.

Generally, where fragments, variants, or derivatives of a lysin polypeptide isolated from phage F87s/06 are concerned, 'antimicrobial activity' or 'antibiotic activity' refers to both functionalities, that is, to the catalytic and targeting activities to bring about cell death of gram-positive bacteria, e.g., *S. aureus*, the native host for phage F87s/06. Where fragments, variants, or derivatives of a lysin polypeptide isolated from phage F170/08 or F168/08 are concerned, 'antimicrobial activity' or 'antibiotic activity' refers to only the catalytic activity to bring about host cell death, e.g., when said fragment is otherwise targeted to the host cell.

In one aspect, this invention is directed to polypeptides isolated from a phage that infects gram-positive bacteria. The polypeptides have antimicrobial (e.g., lytic) and/or targeting activity against one or more strains of *Staphylococcus aureus*. In one embodiment, polypeptides are provided that exhibit antimicrobial and/or targeting activity against methicillin resistant strains of *Staphylococcus aureus* (MRSA). In addition, polypeptides having antimicrobial and/or targeting activity against one or more bacterial pathogens such as *Staphylococcus epidermidis, S. auricularis, S. capitis, S. haemolyticus, S. hominis, S. saprophyticus, S. simulans, S. xylosis, Micrococcus luteus, Bacilus subtilis, B. pumilus, Enterococcus faecalis, E. hirae, E. laecium* and *E. avium* are provided herein.

Preferably, the polypeptide of the invention is isolated from bacteriophage F87s/06, which infects the host *S. aureus*. In one embodiment, the polypeptide comprises an amino acid sequence having at least 60%, 65%, 70%, 75%, 80%, 85%, 95%, 90%, 95%, 96%, 97%, 98%, 99%, or greater sequence identity to SEQ ID NO: 2, which polypeptide exhibits antibiotic and/or targeting activity against *S. aureus*. Sequence identity with respect to the polypeptide sequences disclosed herein is defined as the percentage of amino acid residues that are identical in a candidate sequence of the same length (i.e., consists of the same number of residues) as the amino acid sequences of the present invention. The present invention also encompasses variants, derivatives and/or fragments of SEQ ID NO: 2 retaining antimicrobial activity and/or targeting activity.

In another aspect, this invention is directed to isolated polypeptides of the present invention recombinantly fused or chemically conjugated (including both covalently and non-covalently conjugations) to therapeutic agents, e.g., small molecules or heterologous polypeptides, to generate fusion proteins or chimeric polypeptides. The fusion does not necessarily need to be direct, but may occur through linker sequences or through chemical conjugation. Non-limiting examples of therapeutic agents to which the polypeptides of the invention may be conjugated are peptide or non-peptide cytotoxins (including antimicrobials and/or antibiotics), tracer/marker molecules (e.g., radionuclides and fluorophore) and other antibiotic compounds as known in the art.

In a particular embodiment, the invention in directed to chimeric polypeptides where at least one domain of a polypeptide isolated from phage F87s/06, or a fragment thereof, is substituted with at least one domain of a heterologous protein. Preferable chimeric constructs include the substitution of a catalytic domain of a lysin isolated from phage F87s/06 (Lys 87) with a corresponding domain of a lysin isolated from phage F170/08 or F168/08 (Lys170 or Lys168), which infect hosts of the *Enterococcus* species. The resulting chimeric lysin constructs are renamed Lys170-87 and Lys168-87, respectively. Preferably. Lys 170-87 comprises a targeting domain of a Lys 87 and a catalytic domain of Lys 170; whereas Lys 168-87 comprises a targeting domain of Lys 87 and a catalytic domain of Lys 168. The targeting domain of Lys 87 can correspond to the cell wall binding domain of the lysin polypeptide. 'Targeting domain' as used herein refers to a functional domain of a lysin polypeptide capable of directing the lysin polypeptide to a host cell, e.g., *S. aureus*, thereby facilitating lytic action upon the host cell. As used herein, 'lysin' is used interchangeably with 'endolysin.'

In one embodiment, the chimeric polypeptides Lys170-87 and Lys 168-87 comprise an amino acid sequence having at least 60%, 65%, 70%, 75%, 80%, 85%, 95%, 90%, 95%, 96%, 97%, 98%, 99%, or greater sequence identity to SEQ ID NO: 4 or SEQ ID NO: 6, respectively, which chimeric polypeptide exhibits antibiotic or antimicrobial activity against *S. aureus*. Sequence identity with respect to the chimereic polypeptide sequences disclosed herein also is defined as the percentage of amino acid residues that are identical in a candidate sequence of the same length (i.e., consists of the same number of residues) as the amino acid sequences of the present invention. The present invention also encompasses variants, derivatives and/or fragments of SEQ ID NO: 4 and SEQ ID NO: 6 retaining antimicrobial activity and/or antibiotic activity. In particularly preferred embodiments, the chimeric polypeptides and variants, derivatives, and/or fragments thereof improve the properties of Lys 87 in terms of increased solubility, yield, stability and/or lytic performance.

Antibiotic Compositions

The isolated and chimeric polypeptides of the present invention may be administered alone or incorporated into a pharmaceutical composition for the use in treatment or prophylaxis of bacterial infections caused by gram-positive bacteria, including *Staphylococcus aureus*. In such embodiments, the pharmaceutical composition may be an antibiotic composition. The polypeptides may be combined with a pharmaceutically acceptable carrier, excipient, or stabilizer. Examples of pharmaceutically acceptable carriers, excipients and stabilizers include, but are not limited to, buffers such as phosphate, citrate, and other organic acids; antioxidants including ascorbic acid: low molecular weight polypeptides; proteins, such as serum albumin and gelatin; hydrophilic polymers such as polyvinylpyrrolidone; amino acids such as glycine, glutamine, asparagine, arginine or lysin; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ as known in the art. The pharmaceutical composition of the present invention (e.g., antibiotic composition) can also include a lubricant, a wetting agent, a sweetener, a flavoring agent, an emulsifier, a suspending agent, and a preservative, in addition to the above ingredients.

A polypeptide of the present invention may also be combined with one or more therapeutic and/or prophylactic agents useful for the treatment of infection with gram-positive bacteria (e.g. one or more antibiotics and/or lysins as are known in the art). Therapeutic agents that may be used in combination with the polypeptide of the invention include standard antibiotics agents, anti-inflammatory agents, and antiviral agents.

Standard antibiotics that maybe used with pharmaceutical compositions comprising polypeptides of the invention include, but are not limited to, amikacin, gentamicin, kanamycin, neomycin, netilmicin, paromomycin, rhodostreptomycin, streptomycin, tobramycin, apramycin, rifamycin, naphthomycin, geldanamycin, ansamitocin, carbacephems, imipenem, meropenem, ertapenem, faropenem, doripenem, panipenem/betamipron, biapenem, PZ-601, cephalosporins, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, azithromycin, clarithromycin, dirithromycin, erythromycin, roxithromycin, aztreonam, pencillin and penicillin derivatives, actinomycin, bacitracin, colistin, polymyxin B, cinoxacin, flumequine, nalidixic acid, oxolinic acid, piromidic acide, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, garenoxacin, gemifloxacin, stifloxacin, trovalfloxacin, prulifloxacin, acetazolamide, benzolamide, bumetanide, celecoxib, chlorthalidone, clopamide, dichlorphenamide, dorzolamide, ethoxyzolamide, furosemide, hydrochlorothiazide, indapamide, mafendide, mefruside, metolazone, probenecid, sulfacetamide, sulfadimethoxine, sulfadoxine, sulfanilamides, sulfamethoxazole, sulfasalazine, sultiame, sumatriptan, xipamide, tetracycline, chlortetracycline, oxytetracycline, doxycycline, lymecycline, meclocycline, methacycline, minocycline, rolitetracycline and any combination thereof. In certain embodiments, the combination of one or more polypeptides of the invention and one or more antibiotics as known in the art may enhance (e.g., additively or synergistically) the therapeutic effect of the polypeptide of the invention for a given infection.

The chimeric polypeptides of the present invention comprise a combination where heterologous lysins are recombinantly fused, preferably where a catalytic domain of a lysin isolated from phage F87s/06 is substituted with a catalytic domain of a lysin from either phage F170/08 or F168/08. Preferably, the lysin construct comprises a targeting domain of the lysin from phage F87s/06 and a catalytic domain from the lysin from phage F170/08 or F168/08, which natively infect *Enterococcus* species. Without wishing to be bound by theory, it is believed that the chimeric construct in accordance with the instant invention targets gram-positive bacteria, including *Staphylococcus aureus*, the native host for phage F87s/06, based on the phage F87s/06 lysin targeting domain, whereupon the phage F170108 or F168/08 catalytic domain destroys the host cell wall, causing lysis and bacterial death. That is, the constructs permit lysins that natively act on one species. *Enterococcus*, to exert antimicrobial action on other species, such as *Staphylococcus aureus*. Accordingly, the present invention provides chimeric lysin constructs that permit species cross-reactivity in accordance with a goal of the invention. In some particularly preferred embodiments, this cross-reactivity serves to improve the lytic performance of the chimeric polypeptides on certain gram-positive bacteria, including *Staphylococcus aureus*, compared to the lytic activity of Lys 87.

The polypeptides of the present invention also may be combined with one or more lysins isolated from a bacteriophage other than bacteriophage F87s/06 and/or other than bacteriophage F170/08 and F168/08. Lysins, in general, either have amidase, endopeptidase, muramidase or glucosaminidase activity. Therefore, the combination of lysins, especially those of different enzymatic activities, is contemplated by the presented invention.

The pharmaceutical compositions can be administered by inhalation, in the form of a suppository or pessary, topically (e.g., as a lotion, solution, cream, ointment or dusting powder), epidermally (e.g., by use of a skin patch), orally (e.g., as a tablet (e.g., containing excipients such as starch or lactose), capsule, ovule, elixir, solution or suspension optionally containing flavoring or coloring agents and/or excipients), or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For topical application to the skin, the polypeptides of the present invention may be combined with one, or a combination of carriers, which include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose cannel, and combination thereof. A topical mode of delivery may include a smear, a spray, a time-release patch, a liquid absorbed wipe, and combinations thereof. The polypeptide of the invention may be applied to a patch either directly or in one of the carriers. The patches may be damp or dry, wherein the lysin or chimeric lysin is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament.

As indicated, the therapeutic agent of the present invention can be administered intranasally or by inhalation and is conveniently delivered in the form of a dry powder inhaler or an aerosol spray presentation from a pressurized container, pump, spray or nebuliser with the use of a suitable propellant, e.g. dichlorodifluoromethane, trichlorofluoromethane, dichlorotetrafluoroethane, a hydrofluoroalkane such as 1,1,1, 2-tetrafluoroethane (HFA 134A™) or 1,1,1,2,3,3,3-heptafluoropropane (HFA 227EA™), carbon dioxide or other suitable gas. In the case of a pressurized aerosol, the dosage unit may be determined by providing a valve to deliver a metered amount. The pressurized container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

For administration in the form of a suppository or pessary, the therapeutic compositions may be applied topically in the form of a gel, hydrogel, lotion, solution, cream, ointment or dusting powder. The therapeutic agent of the present invention may also be dermally or transdermally administered, for example, by the use of a skin patch. They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For administration in tablet form, the tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Dosages and desired drug concentrations of the pharmaceutical compositions of the present invention may vary depending on the particular use. The determination of the appropriate dosage or route of administration is well within the skill of an ordinary physician. Animal experiments can provide reliable guidance for the determination of effective doses in human therapy. Interspecies scaling of effective doses can be performed by one of ordinary skill in the art following the principles described by Mordenti, J. and Chappell, W., 'The use of interspecies scaling in toxicokinetics' in *Toxicokinetics and New Drug Development*, Yacobi et al., Eds., Pergamon Press, New York 1989, pp 42-96 (hereby incorporated by reference in its entirety).

Therapeutic Use

The polypeptides of the present invention have antibiotic activity against a number of gram-positive bacteria, including *Staphylococcus aureus*, and including many methicillin resistant strains of *Staphylococcus aureus*. Therefore, the polypeptides of the present invention may be used in methods of treating infections associated with bacteria against which it has lytic activity (e.g., antibiotic or antimicrobial activity) in both humans and animals. In one embodiment, compositions of the present invention may be used to treat an infection caused by one or more of the following *Staphylococcus aureus, S. epidermidis, S. auricularis, S. capitis, S. haemolyticus, S. hominis, S. saprophyticus, S. simulans, S. xylosis, Micrococcus luteus, Bacilus subtilis, B. punzilus, Enterococcus faecalis, E. hirae*, and *E. faecium*. In certain embodiments, the polypeptides of the invention may also exhibit antibiotic or antimicrobial activity (e.g., lytic killing activity) again Gram-negative bacteria or bacteria that are not classified as either Gram-positive or Gram-negative. In such embodiments, the polypeptides of the invention may be used to treat or manage infections associated with non-Gram-positive bacteria.

Examples of diseases that are caused by infection of gram-positive bacteria that may be treated with pharmaceutical compositions of the present invention include, but are not limited to, post-operative endophtalmitis, endocarditis, infections of the central nervous system, wound infections (e.g., diabetic foot ulcers), pneumonia, osteomylelitis, sepsis, mastitis and meningitis.

Disinfectant and Anti-infective Use

Nearly all bacterial pathogens infect at a mucous membrane site (upper and lower respiratory, intestinal, urogenital and ocular). The mucous membranes themselves are often the reservoir, sometimes the only reservoir for many pathogenic bacteria found in the environment (e.g. pneumococci, staphylococci and streptococci). There are very few anti-infectives that are designed to control the carrier state of pathogenic bacteria. However, studies have shown that by reducing or eliminating this reservoir in environments such as hospitals and nursing homes, the incidence of infections by these bacteria will be markedly reduced.

The polypeptides of the present invention may be used in anti-infective compositions for controlling gram-positive bacteria, including *S. aureus*, in order to prevent or reduce the development of serious infections. In addition to use in compositions for application to mucous membranes, the lysin or lysin construct of the present invention may also be incorporated into formulations such as sprays or ointments for controlling colonization of Gram-positive bacteria on the skin and other solid surfaces.

Diagnostic Methods

The present invention also encompasses diagnostic methods for determining the causative agent in a bacterial infection. In one embodiment, the method comprises culturing bacteria isolated from a bacterial infection and measuring the susceptibility to the antimicrobial peptides of the present invention, wherein susceptibility to the polypeptide indicates the presence of Gram-positive bacteria and the lack of susceptibility indicates the presence of non-responsive bacteria (e.g., non-responsive Gram-negative or non-responsive Gram-positive bacteria).

Amino Acid Variants

The invention also encompasses variants of the lysin polypeptides, or active fragments or derivatives thereof, isolated from bacteriophage F87s/06. In certain embodiments, the invention encompasses an amino acid sequence variant of SEQ ID NO:2, or active fragment or derivative thereof. Amino acid sequence variants of the polypeptides of the invention can be created such that they are substitutional, insertional or deletion variants. Deletion variants lack one or more residues of the native protein which are not essential for function (e.g., antimicrobial and/or targeting activity). Insertional mutants typically involve the addition of material at a nonterminal point in the polypeptide. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine;

threonine to serine; tryptophan to tyrosine; tyrosine to tryptophan or phenylalanine; and valine to isoleucine or leucine.

Once general areas of the gene are identified as encoding the particular lysin protein, or active fragment, as described herein, point mutagenesis may be employed to identify with particularity which amino acid residues are important in the antibiotic activities. Thus, one of skill in the art will be able to generate single base changes in the DNA strand to result in an altered codon and a missense mutation.

Preferably, mutation of the amino acids of a protein creates an equivalent, or even an improved, second-generation molecule. For example, certain amino acids may be substituted for other amino acids in a protein structure without detectable loss of function (e.g., antibiotic and/or targeting activity). In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, interaction with a peptidoglycan within the outer coat of a Gram-positive bacteria. Each amino acid has been assigned a hydropathic index on the basis of their hydrophobicity and charge characteristics; for example: isoleucine (+4.5); valine(+4.2); leucine(+3.8); phenylalanine(+2.8); cysteine/cystine(+2.5); methionine(+1.9); alanine(+1.8); glycine(−0.4); threonine(−0.7); serine(−0.8); tryptophan 0.9); tyrosine(−1.3); proline(−1.6); histidine(−3.2); glutamate(−3.5); glutamine(−3.5); aspartate (−3.5); asparagine (−3.5); lysine (−3.9); and arginine (−4.5). It is also understood in the art that the substitution of like amino acids can be made effectively on the basis of hydrophilicity. Like hydrophobicity, values of hydrophilicity have been assigned to each amino acid: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). Equivalent molecules may be obtained by substitution of one amino acid for another where their hydrophilicity indices are within ±2, preferably ±1, or most preferably ±5 of each other.

Chimeric Constructs

The invention also encompasses chimeric polypeptides derived from bacteriophage F87s/06, which chimeric polypeptides exhibit antibiotic activity against a Gram-positive bacterium, e.g., S. aureus. The chimeric polypeptide may be derived from a lysin isolated from phage F87s/06, or fragment or variant thereof, which is recombinantly fused to a heterologouos lysin. In a particular embodiment, the invention in directed to chimeric polypeptides where at least one domain of a lysin isolated from phage F87s/06, or fragment or variant thereof, is substituted with at least one domain of a heterologous lysin, or a fragment or variant thereof. Preferable chimeric constructs include the substitution of a catalytic domain of a lysin isolated from phage F87s/06 (Lys 87) with a corresponding catatlytic domain of a lysin isolated from either phage F170/08 or F168/08 (Lys170 or Lys168), which has antimicrobial or antibiotic activity against S. aureus. Even more preferably, the chimeric lysin comprises a targeting domain of Lys 87 recombinantly fused to a catalytic domain of Lys 170 or of Lys 168.

In certain embodiments, the chimeric polypeptide comprises the amino acid sequence SEQ ID NO:4 or SEQ ID NO:6, or a fragment of either having antimicrobial or antibiotic activity against S. aureus. In other embodiments, the chimeric polypeptide comprises a fragment, variant or derivative of SEQ ID NO:4 or 6, wherein the fragment, variant or derivative has antibiotic activity or antimicrobial activity against a Gram-positive bacteria, e.g., S. aureus. Amino acid sequence variants of the chimeric polypeptides of the present invention can be created as described above with respect to isolated polypeptides of the invention, for example, by substitutions, insertions, deletions, and the like, preferably to generate further improved second- (or third- or more) generation molecules. In particularly preferred embodiments, the chimeric polypeptides and variants, derivatives, and/or fragments thereof, show improved properties with respect to increased solubility, yield, stability and/or lytic performance, compared to the native isolated polypeptide.

Combinatorial Therapy

The present invention further provides compositions comprising one or more polypeptides of the invention and one or more differing prophylactic or therapeutic agents, and methods for treatment of bacterial infection in a subject in need thereof. e.g., preventing, treating, delaying the onset of, slowing the progression of or ameliorating one or more symptoms associated with an infection by gram-positive bacteria) comprising administering to said subject one or more of said compositions. Therapeutic or prophylactic agents include, but are not limited to, peptides, polypeptides, fusion proteins, nucleic acid molecules, small molecules, mimetic agents, synthetic drugs, inorganic molecules, and organic molecules. Any agent which is known to be useful, or which has been used or is currently being used for prevention or treatment of infection by a gram-positive bacteria or for the prevention, treatment or amelioration of one or more symptoms associated with an infection by a gram-positive bacteria, can be used in combination with the antibiotic or antimicrobial polypeptide in accordance with the invention described herein.

In certain embodiments, 'in combination' refers to the use of a fusion protein or chimeric polypeptide, wherein an isolated polypeptide of the invention is covalently or non-covalently joined to another polypeptide, as described above. Preferable fusion proteins include chimeric polypeptides of Lys87 with one or more heterologous lysins, such as Lys 170 or Lys168 from Enterococcus sp. phages. Substitution of the native Lys87 catalytic domain by the corresponding domain from either Lys 170 or Lys 168 produces Lys170-87 and Lys168-87, respectively. The chimeric constructs show increased lytic performance compared to native Lys87, with respect to Gram-positive bacteria and in particular with respect to S. aureus.

Polynucleotides Encoding Polypeptides

The invention provides polynucleotides comprising a nucleotide sequence encoding a polypeptide of the invention. The invention also encompasses polynucleotides that hybridize under high stringency, intermediate or lower stringency hybridization conditions, to polynucleotides that encode a polypeptide of the invention. 'High stringency conditions' can include, but are not limited to, those that (1) employ low ionic strength and high temperature for washing, for example 0.015 M sodium chloride/0.0015 M sodium citrate/0.1% sodium dodecyl sulfate at 50° C.; (2) employ, during hybridization, a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50

µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. 'Moderately stringent conditions' are described by, but not limited to those in Sambrook et al., Molecular Cloning: A Laboratory Manual. 2.sup.nd Ed., New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C.

The polynucleotides may be obtained, and the nucleotide sequence of the polynucleotides determined, by any method known in the art. For example, a polynucleotide encoding a polypeptide of the invention may be generated from nucleic acid from a suitable source (e.g., bacteriophage F87s/06). If a source containing a nucleic acid encoding a particular polypeptide is not available, but the amino acid sequence of the polypeptide of the invention is known, a nucleic acid encoding the polypeptide may be chemically synthesized and cloned into replicable cloning vectors using methods well known in the art.

Once the nucleotide sequence of the polynucleotide of the invention is determined, the nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning. A Laboratory Manual*, 2d Ed., Cold Spring Harbor Laboratory, Cold Spring Harbor, N.Y. and Ausubel et al. eds., 1998, *Current Protocols in Molecular Biology*, John Wiley & Sons, NY, which are both incorporated by reference herein in their entireties), to generate polypeptides having a different amino acid sequence, for example to create amino acid substitutions, deletions, and/or insertions.

Chimeric polynucleotides of the invention encompass nucleotide sequences encoding chimeric polypeptide of the invention, such as chimeric polypeptides comprising a targeting domain of a lysin isolated from phage F87s/06 fused to a catalytic domain of a lysin isolated from phage F170/08 or F168/08. The invention also encompasses polynucleotides that hybridize under high stringency, intermediate or lower stringency hybridization conditions, e.g., as defined supra, to chimereic polynucleotides that encode a chimeric polypeptide of the invention Chimeric polynucleotides may be obtained by recombinant techniques, as are well known and routinely practiced in the art. Recombinant chimeric polynucleotides typically are created by joining two or more genes, or portions thereof, which originally coded for separate proteins. The individual sequences typically correspond to coding sequences for a functional domain of each of the respective proteins, such that the chimeric polypeptide encodes a fusion protein having dual functionality. For example, a first coding sequence, or portion thereof, may be joined in frame to a second coding sequence, or portion thereof, which typically is achieved through ligation or overlap extension PCR. Ligation is used with the conventional method of creating chimeric genes, called the 'cassette mutagenesis method.' In this method, DNA can be cut into specific fragments by restriction endonucleases acting at restriction endonuclease recognition sites, and the specific fragments can be then ligated. A particular fragment can be substituted with a heterologous one having compatible ends in order to ligate it into the parental DNA. See, e.g., Wells et al., Gene 34:315-23 (1985), hereby incorporated by reference in its entirety.

Alternatively, various approaches involving PCR may be used, such as the overlap extension PCR method. See, e.g., Ho. S, N., et al (1989). Site-directed mutagenesis by overlap extension using the polymerase chain reaction. Gene. 77: 51-59, hereby incorporated by reference in its entirely. Several variations of this PCR approach are known and have been used to generate chimeras. One such approach, for example, involves modified overlap extension PCR to create chimeric genes in the absence of restriction enzymes in three steps: (i) a conventional PCR step, using primers partially complementary at their 5' ends to the adjacent fragments that are to be fused to create the chimeric molecule; (ii) a second PCR step where the PCR fragments generated in the first step are fused using the complementary extremities of the primers; and (iii) a third step involving PCR amplification of the fusion product. The final PCR product is a chimeric gene built up with the different amplified PCR fragments. See, e.g., Wurch, T. et al (1998) A modified overlap extension PCR method to create chimeric genes in the absence of restriction enzymes. Biotechnology Techniques. 12(9):653-657, hereby incorporated by reference in its entirety. Any ligation and/or PCR-based recombinant approaches may be used to create the chimeric polynucleotides of the present invention.

Alternatively a nucleic acid encoding the chimeric polypeptide may be chemically synthesized. For example, using the desired amino acid sequence of the chimeric polypeptide of the invention, the corresponding nucleotide sequence may be devised, chemically synthesized, and cloned into replicable cloning vectors using, e.g., well known methods in the art.

Recombinant Expression of Molecules of the Invention

Once a nucleic acid sequence encoding a molecule of the invention (e.g., a polypeptide or bacteriophage origin, or active derivative, chimeric construct, variant or fragment thereof) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al. eds., 1998, *Current Protocols in Molecular Biology*, John Wiley & Sons, NY).

An expression vector comprising the nucleotide sequence of a molecule identified by the methods of the invention can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter. In specific embodiments the expression vector is pQE-30 (Qiagen) or pET-29(a) (Novagen).

The host cells used to express the molecules identified by the methods of the invention may be either bacterial cells (non susceptible to the lysin protein, lysin construct, or fragment thereof of the invention) such as *Escherichia coli*. A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria that are not susceptible to the lysin protein, lysin construct, or fragment of the invention (e.g., *E. coli* and *B. subtilis*) transformed with recombinant bacteriophage DNA, plasmid DNA or cosmid DNA expression vectors containing coding sequences for molecules encompassed by the invention; yeast (e.g. *Saccharomyces Pichia*) transformed with recombinant yeast expression vectors containing sequences encoding molecules encompassed by the invention; insect cell systems infected with recombinant virus expression vectors (e.g., baculovirus) containing the sequences encoding molecules encompassed by the invention; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing sequences encoding molecules encompassed by the invention; or mammalian cell systems (e.g.; COS, CHO, BHK, 293, 293T, 3T3 cells, lymphatic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter)).

In bacterial systems not susceptible to the lysin protein, lysin construct, or fragment of the invention, a number of expression vectors may be advantageously selected depending upon the use intended for the molecule being expressed. For example, when a large quantity of such a protein is to be produced, for the generation of pharmaceutical compositions of a polypeptide, vectors which direct the expression of high levels of fusion protein products that are readily purified may be desirable. Such vectors include, but are not limited to, the *E. coli* expression vector pUR278 (Ruther et al., 1983, *EMBO J.* 2:1791, hereby incorporated by reference in its entirety), in which the protein sequence may be ligated individually into the vector in frame with the lac Z coding region so that a fusion protein is produced; pIN vectors (Inouye & Inouye, 1985, *Nucleic Acids Res.* 1.3:3101-3109; Van Heeke & Schuster, 1989, *J. Biol. Chem.* 24:5503-5509; each of which is hereby incorporated by reference in its entirety); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The polypeptide coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the polypeptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the polypeptide molecule in infected hosts (e.g., see Logan & Shenk, 1984, *Proc. Natl. Acad. Sci.* USA 81:355-359, hereby incorporated by reference in its entirety). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, Bittner et al., 1987, *Methods in Enzymol.* 153:51-544, hereby incoporated by reference in its entirety).

For long-term, high-yield production of recombinant proteins, stable expression is preferred. For example, cell lines which stably express a polypeptide of the invention may be engineered. Rather than using expression vectors which contain viral origins of replication, host cells can be transformed with DNA controlled by appropriate expression control elements (e.g. promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides of the invention. Such engineered cell lines may be particularly useful in screening and evaluation of bacterial species susceptible to the polypeptides of the invention.

A number of selection systems may be used, including but not limited to the herpes simplex virus thymidine kinase (Wigler et al. 1977, *Cell* 11: 223), hypoxanthineguanine phosphoribosyltransferase (Szybalska & Szybalski, 1992, *Proc. Natl. Acad. Sci. USA* 48: 202), and adenine phosphoribosyltransferase (Lowy et al., 1980, *Cell* 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78: 1527); gpt, which confers resistance to mycophenolic acid (Mulligan & Berg. 1981, *Proc. Natl. Acad. Sci. USA* 78:2072): neo, which confers resistance to the aminoglycoside G-418 (*Clinical Pharmacy* 12: 488-505; Wu and Wu, 1991, 3:87-95; Tolstoshev, 1993, Ann. Rev. Pharmacol. Toxicol. 32:573-596; Mulligan. 1993, *Science* 260:926-932; and Morgan and Anderson, 1993, *Ann. Rev. Biochem.* 62:191-217: May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY: and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1; and hygro, which confers resistance to hygromycin (Santerre et al., 1984, Gene 30:147).

The expression levels of a polypeptide of the invention can be increased by vector amplification (for a review, see Bebbington and Hentschel, *The use of vectors based on gene amplification for the expression of cloned genes in mammalian cells in DNA cloning*, Vol. 3 (Academic Press, New York, 1987). When a marker in the vector system expressing an polypeptide is amplifiable, increase in the level of inhibitor present in culture of host cell will increase the number of copies of the marker gene. Since the amplified region is associated with the nucleotide sequence of the polypeptide, production of the polypeptide will also increase (Crouse et al., 1983, *Mol. Cell. Biol.* 3:257).

Once a molecule of the invention (i.e., a polypeptide) has been recombinantly expressed, it may be purified by any method known in the art for purification of polypeptides, for example, by chromatography (e.g., ion exchange, affinity, and sizing column chromatography), centrifugation, differential solubility, or by any other standard technique for the purification of polypeptides or antibodies.

The following examples illustrate but do not limit the invention. Thus, the examples are presented with the understanding that modifications may be made and still be within the spirit and scope of the invention.

EXAMPLES

Experimental Methods

The following bacterial stains were used for cloning and sequencing purposes, *E. coli* JM 109 and *E. coli* BL21(DE3) pLysE (Novagen, San Diego).

The bacteria were grown in both LB broth (10 g tryptone, 5 g yeast extract, 5 g NaCl, 1 mL of 1N NaOH, in 1 L of distilled water) and LB agar (10 g tryptone, 5 g yeast extract, 5 g NaCl, 15 g of agar in 1 L of distilled water) or 2×YT (16 g tryptone, 1.0 g yeast extract, 5 g NaCl, in 1 L of distilled water) at 37° C. Where necessary, the antibiotics kanamycin and ampicillin were added to the growth medium as selection markers.

Bacteriophage F87s/06 was isolated from a clinical isolate of *Staphylococcus aureus* (isolate number 77 of Table I) by induction with mitomycin.

The expression vectors used were pQE-30 (Qiagen, Hilden. Germany) and pET-29(a) (Novagen). Plasmid maps are represented in FIG. 2 *a*), *b*) and *c*). The recombinant plasmids pQE-30/Lys87 and pET-29(a)/Lys87 used to express the protein of interest were designated pCC1 and pCC2, respectively. The bacterial isolates used in the clinical assays of the present experiment are listed in Table i.

TABLE I

| No. | Species | Provenience | Sample type | Line | Observations |
|---|---|---|---|---|---|
| 1 | *Staphylococcus aureus* | H1 | Purulent Exudates | STA hospital | — |
| 2 | *Staphylococcus aureus* | H2 | Drain Exudate | STA hospital | — |
| 3 | *Staphylococcus aureus* | H2 | Wound exudate | STA hospital | MRSA |
| 4 | *Staphylococcus aureus* | H2 | Wound exudate | STA hospital | MRSA |
| 5 | *Staphylococcus aureus* | H3 | Exudate from Dialysis catheter | STA hospital | — |
| 6 | *Staphylococcus aureus* | H1 | Purulent exudate | STA hospital | — |
| 7 | *Staphylococcus aureus* | H3 | Exudate from Pressure ulcer | STA hospital | MRSA |
| 8 | *Staphylococcus aureus* | H4 | Exudate from Pressure ulcer | STA hospital | — |
| 9 | *Staphylococcus aureus* | H2 | Exudate from skin | STA hospital | MRSA |
| 10 | *Staphylococcus aureus* | H1 | Pus | STA hospital | — |
| 11 | *Staphylococcus aureus* | H5 | Exudates | STA ambulatory | MSSA |
| 12 | *Staphylococcus aureus* | H4 | Exudate from Pressure ulcer | STA hospital | MRSA |
| 13 | *Staphylococcus aureus* | H5 | Exudate from wound | STA hospital | MRSA |
| 14 | *Staphylococcus aureus* | H5 | Exudate from Umbical cord | STA ambulatory | MSSA |
| 15 | *Staphylococcus aureus* | H3 | Exudate from Pressure ulcer | STA hospital | MRSA |
| 16 | *Staphylococcus aureus* | H6 | Exudate from Pressure ulcer | STA ambulatory | MSSA |
| 17 | *Staphylococcus aureus* | H5 | Exudates | STA ambulatory | MRSA |
| 18 | *Staphylococcus* | H4 | Exudate from | STA | MRSA |

TABLE I-continued

| No. | Species | Provenience | Sample type | Line | Observations |
|---|---|---|---|---|---|
| | aureus | | wound | hospital | |
| 19 | Staphylococcus aureus | H5 | Exudates | STA ambulatory | — |
| 20 | Staphylococcus aureus | H5 | Exudate from Skin | STA hospital | — |
| 21 | Staphylococcus aureus | H5 | Abscess exudate | STA ambulatory | — |
| 22 | Staphylococcus aureus | H5 | Exudate from Umbical cord | STA ambulatory | MSSA |
| 23 | Staphylococcus aureus | H5 | Pus | STA ambulatory | MSSA |
| 24 | Staphylococcus aureus | H7 | Pus | STA hospital | — |
| 25 | Staphylococcus aureus | H7 | Pus | STA hospital | — |
| 26 | Staphylococcus aureus | H3 | Phlegmon pus | STA hospital | MRSA |
| 27 | Staphylococcus aureus | H5 | Exudate from Foot | STA hospital | MRSA |
| 28 | Staphylococcus aureus | H4 | Exudate from Pressure ulcer | STA hospital | MRSA |
| 29 | Staphylococcus aureus | H5 | Exudate from ulcer | STA hospital | MRSA |
| 30 | Staphylococcus aureus | H5 | Exudates | STA hospital | MRSA |
| 31 | Staphylococcus aureus | H5 | Exudates | STA hospital | — |
| 32 | Staphylococcus aureus | H5 | Exudates | STA hospital | MRSA |
| 33 | Staphylococcus aureus | H5 | Exudate from wound | STA ambulatory | — |
| 34 | Staphylococcus aureus | H5 | Exudates | STA hospital | — |
| 35 | Staphylococcus aureus | H5 | Exudates | STA ambulatory | MSSA |
| 36 | Staphylococcus aureus | H5 | Exudates | STA hospital | — |
| 37 | Staphylococcus aureus | H5 | Exudates | STA hospital | MSSA |
| 38 | Staphylococcus aureus | H5 | Exudates | STA hospital | MRSA |
| 39 | Staphylococcus aureus | H5 | Exudate from wound | STA hospital | MRSA |
| 40 | Staphylococcus aureus | H5 | Exudates | STA hospital | MSSA |
| 41 | Staphylococcus aureus | H5 | Exudates | STA hospital | MSSA |
| 42 | Staphylococcus aureus | H5 | Exudate from wound | STA hospital | MRSA |
| 43 | Staphylococcus aureus | H5 | Exudates | STA hospital | MRSA |
| 44 | Staphylococcus aureus | H5 | Exudate from wound | STA ambulatory | MRSA |
| 45 | Staphylococcus aureus | H5 | Exudates | STA hospital | MRSA |
| 46 | Staphylococcus aureus | H5 | Cellulitis exudate | STA ambulatory | MSSA |
| 47 | Staphylococcus aureus | H5 | Exudate from wound | | MRSA |
| 48 | Staphylococcus aureus | H5 | Exudates | STA hospital | MSSA |
| 49 | Staphylococcus aureus | H5 | Exudate from wound | STA hospital | MRSA |
| 50 | Staphylococcus aureus | H5 | Exudates | STA hospital | MSSA |
| 51 | Staphylococcus aureus | H5 | Exudate from wound | STA hospital | MRSA |
| 52 | Staphylococcus aureus | H5 | Exudate from wound | | MSSA |
| 53 | Staphylococcus aureus | H8 | Urine | STA ambulatory | — |
| 54 | Staphylococcus aureus | H8 | Urine | STA ambulatory | — |
| 55 | Staphylococcus aureus | H6 | Exudate from ulcer | STA ambulatory | — |
| 56 | Staphylococcus | H2 | Sputum | STA | — |

TABLE I-continued

| No. | Species | Provenience | Sample type | Line | Observations |
|---|---|---|---|---|---|
| | aureus | | | hospital | |
| 57 | Staphylococcus aureus | H2 | Ascites | STA hospital | MRSA |
| 58 | Staphylococcus aureus | H1 | Blood culture | STA hospital | — |
| 59 | Staphylococcus aureus | H2 | Catheter tip | STA hospital | — |
| 60 | Staphylococcus aureus | H2 | Blood culture | STA hospital | R-Oxa |
| 61 | Staphylococcus aureus | H3 | Pus | STA hospital | — |
| 62 | Staphylococcus aureus | H1 | Bronchial aspirate | STA hospital | — |
| 63 | Staphylococcus aureus | H3 | Sputum | STA hospital | MRSA |
| 64 | Staphylococcus aureus | H4 | Exudate from Skin lesion | STA hospital | — |
| 65 | Staphylococcus aureus | H2 | Pus | STA hospital | S-Oxa |
| 66 | Staphylococcus aureus | H4 | Urine | STA hospital | — |
| 67 | Staphylococcus aureus | H2 | Pus | STA hospital | MSSA |
| 68 | Staphylococcus aureus | H2 | Exudate from trochanter | STA hospital | MSSA |
| 69 | Staphylococcus aureus | H1 | Bronchial aspirate | STA hospital | — |
| 70 | Staphylococcus aureus | H5 | Exudate from eye | STA hospital | MRSA |
| 71 | Staphylococcus aureus | H5 | Blood culture | STA hospital | MRSA |
| 72 | Staphylococcus aureus | H4 | Exudate from Pressure ulcer | STA hospital | MRSA |
| 73 | Staphylococcus aureus | H5 | Exudate from skin | STA hospital | MSSA |
| 74 | Staphylococcus aureus | H4 | Sputum | STA hospital | MRSA |
| 75 | Staphylococcus aureus | — | ATCC | ATC | — |
| 76 | Staphylococcus aureus | H8 | Urine | STA ambulatory | — |
| 77 | Staphylococcus aureus | H2 | Synovial fluid | STA hospital | — |
| 78 | Staphylococcus aureus | H6 | Urine | STA ambulatory | — |
| 79 | Staphylococcus epidermidis | H2 | Blood culture | SCN hospital | — |
| 80 | Staphylococcus epidermidis | H3 | Exudate from Dialysis catheter | SCN hospital | — |
| 81 | Staphylococcus epidermidis | H5 | Blood culture | SCN ambulatory | — |
| 82 | Staphylococcus epidermidis | H7 | Urine | SCN hospital | — |
| 83 | Staphylococcus epidermidis | H4 | Urine | SCN hospital | — |
| 84 | Staphylococcus epidermidis | H5 | Catheter | SCN hospital | — |
| 85 | Staphylococcus auricularis | H1 | Blood culture | SCN hospital | — |
| 86 | Staphylococcus capitis | H1 | Pus | SCN hospital | — |
| 87 | Staphylococcus capitis | H5 | Blood culture | SCN ambulatory | — |
| 88 | Staphylococcus capitis | H5 | Drain fluid | SCN hospital | — |
| 89 | Staphylococcus haemolyticus | H1 | Sputum | SCN hospital | — |
| 90 | Staphylococcus haemolyticus | H5 | Catheter tip | SCN hospital | — |
| 91 | Staphylococcus haemolyticus | H7 | Urine | SCN hospital | — |
| 92 | Staphylococcus hominis | H5 | Blood culture | SCN ambulatory | — |
| 93 | Staphylococcus hominis | H4 | Sputum | SCN hospital | — |
| 94 | Staphylococcus | H2 | Urine | SCN | R-Oxa |

TABLE I-continued

| No. | Species | Provenience | Sample type | Line | Observations |
|---|---|---|---|---|---|
| | saprophyticus | | | hospital | |
| 95 | Staphylococcus saprophyticus | H7 | Urine | SCN hospital | Multiresistente |
| 96 | Staphylococcus Saprophyticu | H4 | Urine | SCN hospital | — |
| 97 | Staphylococcus simulans | H1 | Blood culture | SCN hospital | — |
| 98 | Staphylococcus xylosis | H5 | Blood culture | SCN ambulatory | — |
| 99 | Micrococcus luteus | — | ATCC | ATC | — |
| 100 | Bacillus subtilis | — | ATCC | ATC | — |
| 101 | Bacillus pumilus | — | ATCC | ATC | — |
| 102 | E. coli | — | ATCC | ATCC | E. coli ATCC 25922 |
| 103 | Enterococcus faecalis | — | Endometrium | — | — |
| 104 | Enterococcus sp. | H8 | Urine | EN ambulatory | — |
| 105 | Enterococcus hirae | — | CIP | CI | — |
| 106 | Enterococcus faecium | H2 | Urine | EFM hospital | — |
| 107 | Enterococcus avium | H8 | — | ENA ambulatory | — |
| 108 | Streptococcus neumonia | H4 | sputum | STR hospital | — |
| 109 | Streptococcus A | H5 | Pharyngeal exudate | STR hospital | — |
| 110 | Streptococcus B | H5 | Blood culture | STR ambulatory | — |

Table I lists the clinical bacterial isolates used to test the antibacterial activity of SEQ ID NO: 2. The following abbreviations are used: ATCC—American Type Culture Collection; CIP—equivalent of ATCC; ECO—*E. Coli*; EN—*Enterococcus* sp.; ENA—*Enterococcus avium*; EFM—*Enterococcus faecium*; EFS—*Enterococcus faecalis*; MRSA—methicilin resistant *Staphylococcus aureus*; STA—*Staphylococcus aureus*; SCN—*Staphylococcus* Coagulase Negative; STR—*Streptococcus*; R-Oxa—Resistance to oxacilinia; S-Oxa-Senisitive to oxacilina. The bacterial isolates were obtained from a hospital in the Lisbon area, a hospital in Alto Alentejo, and a hospital in Algarve.

Bioinformatic Analysis of the Putative Lysin Protein from Phage F87s/06

Analysis of target DNA and amino acid sequences was carried out by using ExPASy (Expert Protein Analysis System) of the Swiss Institute of Bioinformatics. Additional analysis was also carried out using the programs Translate Tool, Prosite and ProtPram. The homology of the target amino acid sequences with sequences in the UniProt Knowledge base database were performed using FASTA3. Sequence alignments were performed using ClustalW. Both programs can be accessed through the European Molecular Biology Laboratory—European Bioinformatics Institute (EMBL-EBI) website. The determination of the secondary structure of the target sequence was carried using the program FoldIndex.

Purification of Phage F87s/06

A preparation of stock phage F87s/06 was carried out using the protocols described in Carlson K., 2005, 'Working with bacteriophages: common techniques and methodological approaches,' in Kutter, E. Sulakvelidze, A. (eds.) *Bacteriophages: Biology and Applications.* 5th ed. CRC press ('Carlson:' hereby incorporated by reference in its entirety).

The stock phage F87s/06 was concentrated by precipitation with PEG according to the protocol described in Yamamato et al., 2004, *PNAS* 101:6415-6420 (hereby incorporated by reference in its entirety) and Carlson.

The phage F87s/06 stock was incubated in 1 M NaCl for one hour at 4° C. with agitation. Next, PEG 8000 (AppliChem, Cheshire, Mass.) was added gradually until a final concentration of 10% (p/v) was reached. The composition was then incubated overnight at 4° C. After the incubation period the composition was centrifuged at 10000×g for 30 minutes at 4° C. The sediment was then re-suspended in SM (0.05 M Tris-HCl at pH 7.4, 0.1 M NaCl, 10 mM $MgSO_4$ and gelatin at 1% ply) and centrifuged again at 1000 rpm at 4° C. for 10 minutes. The supernatant containing the suspended phage was saved for further purification.

Purification of phage F87s/06 was achieved using a CsCl gradient as described by Carlson.

Removal of CsCl from the phage stock was achieved through dialysis. A dialysis membrane Cellu.Sep H1 High Grade Regenerated Cellulose Tubular Membrane (Cellu.Sep, River Street, USA) was prepared according to the manufacturer's instructions. The dialysis consisted of a first incubation of 30 minutes in 100 mM Tris-HCl and 3 M NaCl (pH 7.4) at 4° C. This was followed by a second incubation of 30 minutes in 100 mM Tris-HCl and 0.3 M NaCl (pH 7.4) at 4° C. After dialysis, the suspended phage was removed from the interior of the dialysis bag and stored at 4° C.

Extraction of Phage DNA

Phage F87s/06 DNA was obtained from the stock phage purified on CsCl. To 5 ml of the purified phage was added 20 mM EDTA at pH 8.0, SDS at 0.5% (p/v) and Proteinase K at a final concentration of 40 μg/ml. The mixture was then incubated at 56° C. for one hour. This was followed by successive extractions in phenol:chloroform:alcohol at a proportions of 25:24:1, until the interface between the aqueous and organic phases was clear. The aqueous phase was then treated with an equal volume of chloroform and centrifuged at 13,0000×g for 10 minutes at 4° C. The aqueous phase was once again removed and the DNA was precipitated by adding two volumes of absolute ethanol and incubating for thirty minutes at 20° C. The samples were then centrifuged at 11,000×g for 30 minutes at 4° C. The pellet was then washed with 70% ethanol at room temperature and re-suspended in 50 µl of ultra-pure water (Gibco, Calif.). The DNA concentration was then determined by measuring the absorbance at 260 nm in a ND-1000 Spectrophotometer. The integrity of the isolated phage DNA was then analyzed by electrophoresis on a 1% agarose gel.

The phage F87s/06 DNA was then sequenced and the open reading frames (ORFs) coding for amino acid sequences were identified using the tools describe under the Bioinfomatics Analysis section. In addition the homology of phage F87s/06 DNA was compared to existing sequences using the program FASTA3.

Preparation of Competent Cells

In order to prepare competent cells, LB broth was inoculated with competent *E. coli* and incubated overnight with agitation of 135 rpm at 37° C. The following day, 5 ml from the cultured LB broth was added to 200 ml of fresh LB broth. The culture was incubated with agitation at 37° C. until an optical density ($OD_{600}$) of 0.7-0.8 was reached. The optical density was measured on a UV/Vis Spectrometer UVA (Unicam). The cells were then centrifuged for 20 minutes at 5,000 rpm at 4° C. After removal of the supernatant, the pellet was re-suspended in 10 ml of a 10% glycerol solution previously cooled in ice. The volume was then brought to 50 ml by adding more of the 10% glycerol solution and centrifuged again at 5,000 rpm for 20 minutes at 4° C. After removal of the supernatant, the pellet was re-suspended as described before and centrifuged an additional time. The pellet was then resuspended in the residual 10% glycerol solution that remained in the tube after decantation. The samples were then aliquoted and stored at −80° C.

Transformation of Competent Cells by Electroporation

In order to a transform the competent *E. coli* cells, an aliquot of competent cells was removed from storage at −80° C. and thawed at 4° C. for 10-20 minutes. Then 1 µl of plasmid DNA was added to 25 µl of competent cells. The suspended cells were then transferred to an electroporation cuvette (Electroporation Cuvettes Plus model No. 610, BTX, Holliston, USA) and electroporated in a Gene Pulser Xcell System (Bio-Rad, Hertfordshire, U.K.). The parameters used for a 1 mm cuvette were as follows: electric impulse—10 µF, Resistance—600 Ohms and Voltage—1.800 V. Immediately after electroporation the cells were resuspended in 1 ml of LB broth and incubated at 37° C. for 1 hour with agitation at 135 rpm. Then the cells were centrifuged at 13,000 rpm for 1 minute at room temperature. The cells were then resuspended in 50 µl of LB broth and plated on a Petri dish containing LB agar (50 µl/plate) and the necessary selective markers. The plates were incubated overnight at 37° C.

Extraction of Plasmid DNA (Minipreps)

After selecting for transformed bacteria, the DNA plasmid of interest was extracted according to the protocol described in Sambrook and Russel, 2001, Molecular cloning: a laboratory manual, $3^{rd}$ ed., Cold Spring Harbor Laboratory Press (hereby incorporated by reference in its entirety). A determination of DNA concentration was then made on a ND-1000 Spectrophotometer by measuring the absorbance at 260 nm. The integrity of the isolated DNA was then analyzed by electrophoresis and visualization on a 1% agarose gel.

Electrophoresis of DNA

Electrophoresis was performed on a 1% agarose gel which is capable of separating fragments between 0.5 and 10 Kb. The agarose was dissolved in TBE 0.5× (108 g Tris, 55 g boric acid, 20 ml of 0.5 M EDTA at pH 8.0 in 1 L of distilled water), followed by the addition of the ethidium bromide at a final concentration of 0.5 pg/ml. DNA samples were prepared for loading onto the gel by addition of 6× loading dye (20% Ficoll 400, 0.1 M $Na_2EDTA$ pH 8.0, 1% SDS, 0.25% bromophenol blue and 0.25% xylene red). Electrophoresis was conducted at 100 mA, for 1 hour in TBE 0.5×. GeneRuler™ 1 kb DNA Ladder Mix (Fermentas, Md., USA) was used to determine the size of the bands after electrophoresis was complete.

Construction of Plasmids

Plasmids pCC1 and pCC2 were constructed by inserting the sequence of cDNA corresponding to the isolated lysin of phage F87s/06 (Lys87) into vectors pQE-30 and pET-29(a). The fragment of DNA corresponding to the gene for the lysin of phage F87s/06 was amplified by PCR using the primers; 87F (CGGGATCCAAAACATACAGTG. SEQ ID NO:3) and 87R (CTAAGAAGCTTAAAACACTTCTTT, SEQ ID NO:4); 87F and 87R1 (CGCTCGAGAAACACTTCTTTCAC, SEQ ID NO:5), respectively. The PCR reaction was set up using the following conditions: puReTaq Ready-to-Go PCR Beads (Amersham Biosciences, U.K.), 200 ng of genomic DNA from phage F87s/06, the primers at a final concentration of 0.4 pmol/µl and ultra-pure water to a final volume of The following thermocycler conditions were used: 1 minute at 95° C. for 1 cycle, 1 minute at 95° C.+1 minute at 57° C.+1 minute at 72° C. for 30 cycles and 5 minutes at 72° C. for one cycle.

The vectors pQE-30 and pET-29(a) were digested with restriction enzymes Bam HI, Hind III and Bam HI and Xho I (Fermentas), respectively. The restriction digest mixture was prepared according to the manufacturer's instructions. The fragment of DNA resulting from the digestion of the vectors as well the amplified DNA of Lys87 were run on a 1% agarose gel. The DNA was then purified from the gel using the High Pure PCR Product Purification Kit (Roche, Germany) according to the manufacturer's instructions.

The purified vector DNA and the cDNA encoding the Lys87 were combined in a ratio of 1:5 moles along with 1 of T4 DNA ligase (New England Biolabs, Frankfort, Germany) 10× ligation buffer (50 mM Tris-HCl, 10 mM $MgCl_2$, 10 mM DTT, 1 mM ATP, pH 7.5 at 25° C.) and ultra-pure water at a final volume of 20 µl. The ligation mixture was incubated overnight at 22° C. followed by transformation of *E. coli* strain JM109 and BL21(DE3)pLysE. The transformation was done according to the protocol described previously.

Transformants were selected by plating in a Petri dish containing LB agar and the respective selection marker. Colonies of transformants containing pCC1 and pCC2 detected on the Petri dish were the used to inoculate LB broth containing the appropriate selection marker and incubated overnight. The cultures where then centrifuged and the DNA extracted as described previously.

Correct insertion of the cloned fragment was determined by digestion of the recombinant plasmid using the same restriction enzymes used to construct the plasmids. All methods and procedures for cloning the Lys87 fragment were done according to standard protocols.

Sequencing

Recombinant plasmids containing the DNA of interest corresponding to the DNA of Lys 87 were sequenced by Macrogen (Coreia do Sul).

Expression and Determination of the Solubility of Lys87

To express Lys87, the JM109 and BL32(DE3)pLysE transformed with pCC1 and pCC2, respectively, were used to inoculate 5 ml of 2×YT broth containing the appropriate selection markers. The cultures were incubated overnight at 37° C. with agitation until a OD (600 nm) of 0.6 was obtained. Expression of the lysin was induced by the addition of 1 mM to 0.5 mM of IPTG. This was done approximately after incubation for 4 hours at 37° C. with agitation. Samples of *E. coli* JM109 (pCC1) were taken at 0, 1, 2, 3 and 4 hours from the point of induction. Samples of *E. coli* BL21(DE3)pLysE (pCC2) were taken at 0, 2 and 4 hours from the point of induction.

After incubation was complete, lysis of the *E. coli* JM109 cells was achieved by the addition of lysosyme (Sigma-Aldrich) at a final concentration of 0.1 mg/ml and 1 µl of Protease Inhibitor Cocktail Set I (Calbiochem, USA) followed by freezing and thawing. The sample was exposed to five cycles of freezing and thawing. The sample was then centrifuged at 14,0000×g for 10 minutes at 4° C. After centrifugation the supernatant was removed and the pellet re-suspended in 500 to of PBS1×.

In order to lyse the *E. coli* BL21(DE3)pLysE (pCC2), the sample was centrifuged at 13,200 rpm for 10 minutes at 4° C. The supernatant was removed and the pellet was re-suspended in 150 µl of BugBuster Master Mix (Novagen) in addition to 1 µl of Protease Cocktail Inhibitor Set I. Lysis of the cells was carried out using the BugBuster Master Mix according the manufacturers instructions. After lysis, 500 µl of each sample was centrifuged at 14,000×g, for 10 minutes at 4° C. After centrifugation, the supernatants was removed and the pellet resuspended in 500 µl of PBS 1×.

All of the samples were analyzed by SDS-PAGE and Western blot in order to determine the activity of Lys87.

SDS-PAGE

In this work, 15% polyacrylamide gels were used. The resolving gel was prepared by adding 6.25 ml Protogel, 3.35 ml Protogel Resolving Buffer (National Diagnostics, Georgia, USA). The stacking gel was prepared using 650 Protogel, 1.25 ml Protogel Stacking Buffer (National Diagnostics). 3 ml distilled water, 50 41. APS 10%, and 7.5 TEMED. Protein samples to be analyzed where then denatured by placing them in 6× denaturing buffer (0.35 M Tris-HCl at pH 6.8, 10.28% DS, 36% glycerol. 0.6 M DTT and 0.012% bromophenol blue) and heated at 100° C. for 10 minutes. The gel was run on a Mini-PROTEAN Tetra Cell (Bio-Rad). While the samples were in the stacking gel the voltage was maintained at 140 V. After the samples entered the resolving gel the voltage was increased to 200 V. Precision Plus Protein™ Standards Dual Color of Bio-Rad and PageRuler™ Prestained Protein Ladder of Fermentas were used as molecular weight ladders.

Transfer to Nitrocellulose Membrane

In order to visualize the protein bands on the SDS-PAGE gel, the gel was immersed in a solution of Coomassie stain for 1 hour at ambient temperature. The gel was then transferred to a destaining buffer (10% acetic acid, 10% methanol in 1 L of distilled water) to remove excess stain.

The gel was then placed in 1× transfer buffer (48 mM Tris, 39 mM glycine, 0.04% SDS, 10% methanol, and IL of distilled water) at ambient temperature. The proteins where then transferred from the gel to a nitrocellulose Hybond C (GE Healthcare, Germany) using a Mini Transblot Module (Bio-Rad). The transfer took place at 200 mA for 1 hour.

Western Blot

The nitrocellulose membrane was the blocked in PBS1×, 5% milk protein, 0.05% TWEEN™ 20 overnight at 4° C. The membrane was then washed 5 times in PBS 1×, 0.05% Tween 20 at room temperature. The membrane was then incubated for 1 hour with agitation at room temperature in a solution containing PBS 1×, 2% milk protein, 0.05% Tween 20 and anti-His6 antibody conjugated to peroxidase diluted 1:5000 (Roche). The membrane was then washed three times for 15 minutes in a solutions of PBS 1×, 0.05% Tween 20 at room temperature.

The protein of interest was detected using the ECL™ Plus Western Blotting Detection System (GE Healthcare) following the manufacturer's instructions. The membrane was then exposed to Amersham Hyperfilm ECL and developed in an AGFA Curix 60 processor.

Evaluation of Lytic Activity of Lys87

Preparation of the bacteria listed in Table I were grown on BHI and incubated with 15 µl of the insoluble fraction from cells expressing Lys87, soluble fraction from cells expressing Lys87, or purified Lys87. A 100 mM Tris-HCl buffer at pH 7.0 was used as a negative control. All of the bacterial isolated, except those belonging to the genus *Streptococcus* where tested by the previous protocol. To test the lytic activity of Lys87 in bacteria from the genus *Streptococcus*, an inoculating loop was used to transfer bacteria from a liquid culture onto a blood agar plate. After plating the *Streptococcus* bacteria, a 15 µl sample of Lys87 in 100 mM Tris-HCl at pH 7.0 was added to the plate and incubated overnight at 37° C.

Preparation of Cell Extracts for the Purification of Lys87

Induction of expression of Lys87 in *E. coli* JN109 (pCC1) was done according to the previously described protocol for hours in a bacterial culture of 500 ml. The bacteria were lysed in a French press at a pressure of 10,000 lb/in$^2$. The cell lysate was then incubated at 4° C. for 30 minutes followed by centrifugation at 4000×g for 10 minutes at 4° C. After centrifugation, the supernatant was retained and used to purify Lys87. A sample was also analyzed by SDS-PAGE and Western Blot.

*E. coli* BL21(DE3)pLysE(pCC2) were prepared according to the previously described protocol. The bacteria where grown until the OD (600 nm) was 0.6, Expression of the lysin was then induced by the addition of 0.5 mM IPTG followed by incubation overnight at 25° C. with agitation. After induction, the liquid cultures were centrifuged at 11,000 rpm for 40 minutes at 4° C. The supernatant was removed and the pellet resuspended in 5 ml of BugBuster Master mix with Protease Inhibitor Cocktail Set I at a dilution of 1:1000. The cells where lysed according to the manufacturer's instructions. The samples were then centrifuged at 4° C. and 14,000×g for 10 minutes. After centrifugation, the supernatant was removed and the pellet re-suspended in 5 ml of PBS 1×. The samples were then centrifuged again at 4° C. and 14,000×g for 10 minutes. The pellet containing inclusion bodies containing Lys87 was stored at 4° C. The samples were analyzed and a Lys87 purified by SDS-PAGE and Western Blot.

Purification of Lys87 using a Ni-NTA column

Lys87 was purified using a Ni-NTA column (Qiagen). The Ni-NTA resin was stored at 4° C. prior to be added to the column. The column was then washed with 50 ml of wash buffer (50 mM Na2HPO$_4$, 300 mM NaCl. 20 mM imidazole in 1 L of distilled water at pH 8.0) using a peristaltic pump at medium speed. The cellular extracts prepared according to the previously described protocols where then loaded onto with a peristaltic pump set at low speed. The column was then washed with 50 ml of washbuffer to remove nonspecific proteins and other impurities. The protein was then eluted from the column using an elution buffer (50 mM Na$_2$HPO$_4$ 300 mM NaCl, 250 mM imidazole in 1 L of distilled water at pH 8.0) and collected in 1.5 ml fractions. All of the fractions were analyzed by SDS-PAGE.

Dialysis of Lys87 Samples Purified by Ni-NTA Chromatography

A Cellu.Sep H1 High Grade Regenerated Cellulose Tubular Membrane was prepared according to the manufacturer's instructions. The samples were dialyzed against 1000 volumes of 50 mM Tris-HCl pH 7.5 overnight at 4° C. with slight agitation. The previous procedure was repeated again until total incubation time reached 24 hours. After dialysis the lysin was removed from the interior of the membrane and stored at 4° C. A sample was analyzed by SDS-PAGE and Western Blot and the amount of protein was quantified using Bradford assay.

Purification of Lys87 from Inclusion Bodies

Inclusion bodies containing Lys87 were resuspended in 10 ml of a Triton X-100 wash buffer (0.5% Triton X-100, 50 mM Tris-HCl pH 8.0, 100 mM NaCl, 0.1% sodium azide in 100 mil of distilled water). The samples were then centrifuged at 15,000 rpm, for 10 minutes at 4° C. The supernatant was removed and the wash steps were repeated seven times. For the final wash the samples were placed in a solution of 50 mM Tris-HCl pH 8.0, 100 mM NaCl and centrifuged at 15,000 rpm for 10 minutes at 4° C. A sample was analyzed by SDS-PAGE and Western Blot.

Denaturation of Lys87 with Urea

The inclusion bodies containing Lys87 were dissolved in a solution of 50 mM Tris-HCl pH 8.0, 100 mM NaCl, 8 M Urea and 100 ml of distilled water and incubated overnight with agitation at 4° C. The following day the samples were centrifuged at 15,000 rpm for 30 minutes at 4° C. The supernatant containing the denatured Lys87 was retained and the amount of protein measured by checking the absorption of the sample at 280 nm. A sample of the supernatant and pellet were both analyzed by SDS-PAGE and Western Blot.

Refolding of Lys87

The denatured Lys87 sample was re-folded by placing the sample in 150 ml of refolding buffer (100 mM Tris-HCl at pH 7.0, 10 mM EDTA at pH 8.0, 5% glycerol, 1 mM DTT, 100 mM NaCl. 0.005% Tween-20 in 200 ml of water). Denatured Lys87 was added to the re-folding buffer drop by drop over a period of approximately 30 minutes. The solution was then incubated 16 to 24 hours at 4° C. The solution was then centrifuged at 15,000 rpm for approximately 30 minutes at 4° C. The supernatant was retained and stored at 4° C. The supernatant was then analyzed by SDS-PAGE and Western Blot. The quantity of Lys87 was determined by measuring the absorbance at 280 nm.

Purification of Lys87 using FPLC

Lys87 expressed from pCC2 was purified from the inclusion bodies using a AKTA FPLC chromatography system (Amersham Biosciences). Prior to purification the sample was denatured according to the previously described protocol. In order to purify the fusion Lys87-His6 protein, a Histrap (GE Healthcare) was used in connection with the AKTA FPLC. Purification of all samples was monitored by measuring the absorbance of the eluate at 280 nm.

Initially the purification column was equilibrated with 10 ml of buffer A (50 mM $Na_3PO_4 12H_2O$, 1 M NaCl. 8 M Urea, 20 mM imidazole). Next, the sample of denatured Lys87 was loaded on the column. The column was then washed with Buffer A containing 60 mM imidazole to remove impurities that had been retained on the column. The lysin was then eluted from the column using a linear gradient of 60 to 500 mM of imidazole in 10 ml increments resulting in collection of 7 fractions of 1.2 ml each. The fractions containing the protein of interest were analyzed with SDS-PAGE and Western Blot.

Concentration of Lys87

The proteins of interest were concentrated on an Amicon Centrifugal Filter Device (Millipore, USA) according to the manufacturer's instructions. The Amicon Centrifugal Filter Devices were also used to exchange the buffer of the protein samples. In this mode, 12 ml of a 100 mM Tris-HCl buffer at pH 7.0 was added together with a sample of Lys87. The column was then centrifuged for 30 minutes at 5,000 rpm at 4° C. Concentrated sample of Lys87 were analyzed by SDS-PAGE and Western Blot in order to confirm the integrity of the purified protein. The concentration of Lys87 was determined using a ND-1000 spectrophotometer measuring the absorbance at 280 nm and using a Bradford assay.

Determination of the Minimum Inhibitory Concentration of Lys87

Isolate 77 of table I was used to determine the minimum inhibitory concentration (MIC) of Lys87 in S. aureus. An isolated colony of isolate 77 was used to inoculate 5 ml of BHI media and incubate overnight at 37° C. with agitation at 135 rpm. Using serial dilutions, it was determined that the mean number of cells was between approximately $10^3$ to $10^4$. Various concentrations of Lys87, ranging from 10 to 100 µg/ml were plated in a 96 well round bottom with lid (Sarstedt. USA). To each well was added 100 µl of bacterial cell culture. A sample comprising only sample buffer and another sample comprising only bacterial culture were used as negative controls. The samples were incubated overnight at 37° C. The next day 15 µl of each sample, including the controls, were spotted on BHIA media plates. The plates were incubated at 37° C. overnight Evaluation of Lytic Activity of Lys87 in Liquid Media.

Evaluation of the lytic activity of Lys87 in liquid media was carried out according to the protocols described in Fischetti. 2003, Ann. NY Acad. Sci. 987:207-214; Loessner et al., 1998. FEMS Microbial. Lett. 162:265-274; Loeffler et al., 2001, Science 294:2170-2172 and Takae et al., 2005, Microbiology 151:2331-2342 (each of which is hereby incorporated by reference in its entirety). S. aureus isolate 77 was used to inoculate 5 ml of B HI media. The culture was allowed to grow overnight at 37° C. with agitation at 135 rpm. The next day the pre-inoculate was used to prepare a liquid culture with an OD) between 0.8 and 1. The decrease in OD was measured after the addition of a determined amount of lysin. Concentrations of Lys87 purified using AKTA FPLC of 50 µg/ml, and 100 µg/ml were tested. Negative controls received an equal volume of 100 mM Tris-HCl at pH 7.0 in place of buffer containing lysin. Lysin or control was added to a 1 ml liquid culture sample with a $OD_{6x}$, between 0.8 and 1. The samples were incubated at 37° C. with gentle agitation and the OD at 600 nm was measured after 2 hours.

Example 1

Isolation and Characterization of Bacteriophage F87s/06

Bacteriophage F87s/06 is a double stranded DNA virus. The virus's genome had not been previously isolated an characterized. Genomic DNA was isolated from a stock of phage F87s/06 obtained from a clinical isolate of Staphylococcus aureus (isolate No. 77 of Table I). The genomic DNA of phage F87s/06 was isolated, cloned, and sequenced according to protocols described in the experimental methods section. Sequencing of the bacteriophage genome allowed identification of potential open reading frames (ORFs) within the genome. The putative ORFs of bacteriophage were translated into their corresponding amino acid sequences and the amino acids sequences were used to search the UniProt Knowledge-base using the program FASTA3. Alignment with other known lysin proteins from other bacteriophages allowed identification of the phage F87s/06 lysin protein (Lys87) (SEQ ID NO: 2) and its corresponding gene sequence (SEQ ID NO:1). Analysis of the amino acid sequence revealed the presence of a CHAP domain. This domain is found in numerous protein sequences and is generally associated with bacterial domains of the SH3 type. The CHAP domain is also known to be associated with endolysins which have been experimentally shown to have endopeptidase and amidase activity against peptidoglycan, FIG. 1 shows an alignment of the N-terminal region of Lys87 with the know lysins of phages P68, Twort and Φ11. The alignment shows that Lys87 shares several conserved residues that are known to be associated with endopeptidase activity.

Example 2

Cloning and Expression of Lys87

Figure 3:
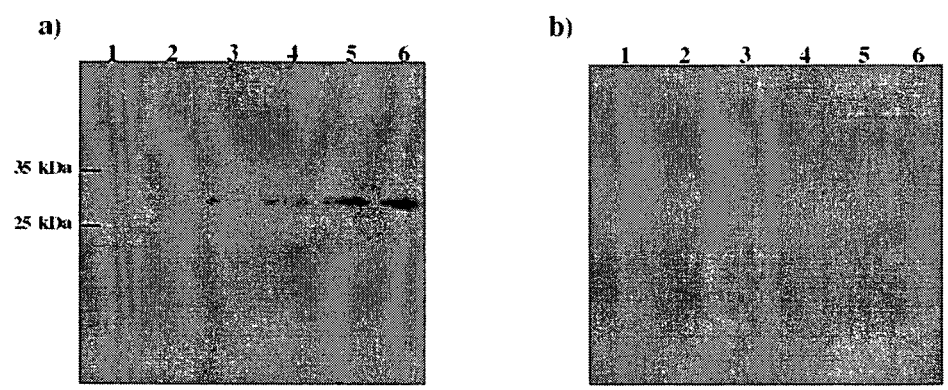
FIGS. 3a and 3b are Western Blots of the insoluble (a) and soluble (b) fractions of cellular extracts resulting from induction of Lys87 expression in *E. coli* JM109 cells transformed with the pCC1 plasmid. The bands were detected using an anti-His6 antibody. Lane 1 represents JM 109 cells without the pCC1 plasmid after 4 hours of induction. Lanes 2-6 correspond to JM109 cells with pCC1 plasmid after 0, 1, 2, 3, and 4 hours of induction.
Figure 4:
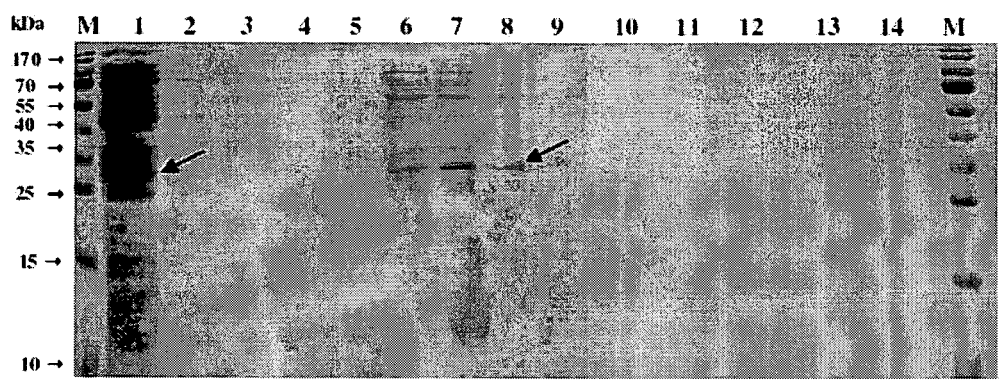
FIG. 4 shows the results of SDS-PAGE of Lys87His6 samples purified on Ni-NTA column after staining with Coomassie blue. Lane 1 represents cellular extract. Lane 2 represents the wash buffer that was passed over the column during purification. Lines 3-14 correspond to fractions collected during purification of the His6-Lys87 fusion protein.

Two different strategies were used based on prokaryotic expression systems utilizing a histidine tail to allow purification of the expressed lysin. FIG. 2 shows a vector map of the two expression vectors used. In the first strategy, the cDNA sequence encoding Lys87 was ligated into the expression vector pQE-30 (pCC1.). As shown in FIG. 3, the results achieved with this expression vector were very low and the lysin itself was insoluble. The results obtain by purification of Lys87His6 using the NiNTAsystem were not satisfactory (FIG. 4). Lastly, the samples of purified Lys87 did not show any lytic activity in strains of *S. aureus*.

Figure 5:
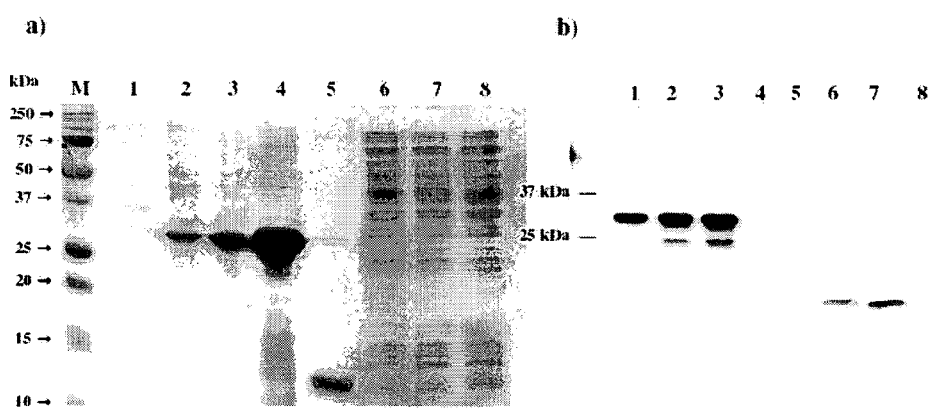
FIGS. 5a and 5b show the soluble and insoluble fractions of cellular extracts resulting from the induction of Lys87 in *E. coli*. BL21(DE3)pLysE transformed with plasmid pCC2 after coloring with Coomassie blue (a) and after immunodetection with anti-His6 antibody (b). Lane 1 represents the insoluble fraction. Lanes 2-4 correspond to the insoluble fraction and lanes 6-8 correspond to the soluble fraction after 0, 2, and 4 hours of induction respectively.
Figure 6:
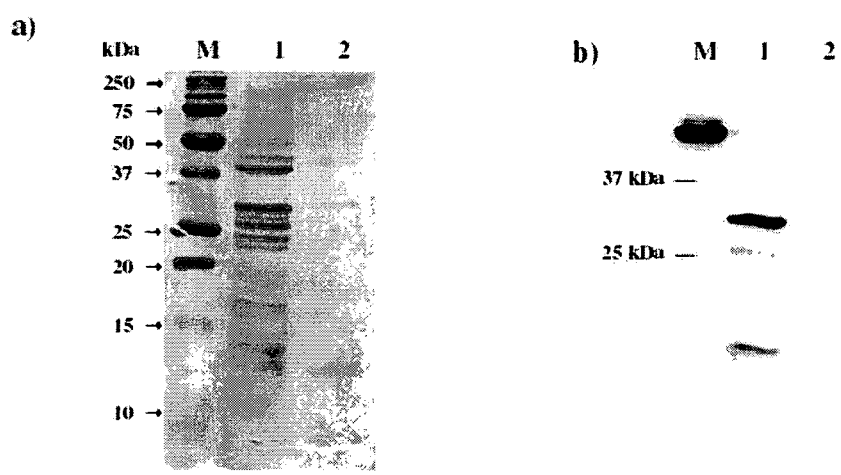
FIGS. 6a and 6b show sample of concentrated and diluted samples of Lys87 after purification from inclusion bodies. Lane 1 corresponds to concentrated Lys87 and lane 2 corresponds to diluted Lys87.

As the previous strategy was not effective, the expression vector and purification strategy were altered. The new expression vector used was pET-29(a) (pCC2) which has a sequence encoding for a tail fusion of 6 histidines to the C-terminal domain of Lys87. This vector also utilizes a T7 promoter for the direct expression of the protein of interest. The use of pCC2 resulted in an increased expression of Lys87 as compared to pCC1 (FIG. 5). While the amount of lysin expression improved significantly, as with the previous strategy, the lysin was expressed in the form of insoluble aggregates or inclusion bodies. In an attempt to solubilize the inclusion bodies and recover the purified protein of interest, the inclusion bodies were solubilized by successive washes, followed by denaturation of the lysin in urea, followed by renaturation and concentration of the protein. As can be observed in FIG. 6, the successive washes of the inclusion bodies, while eliminating some of the undesired proteins, did not remove them totally.

Figure 7:
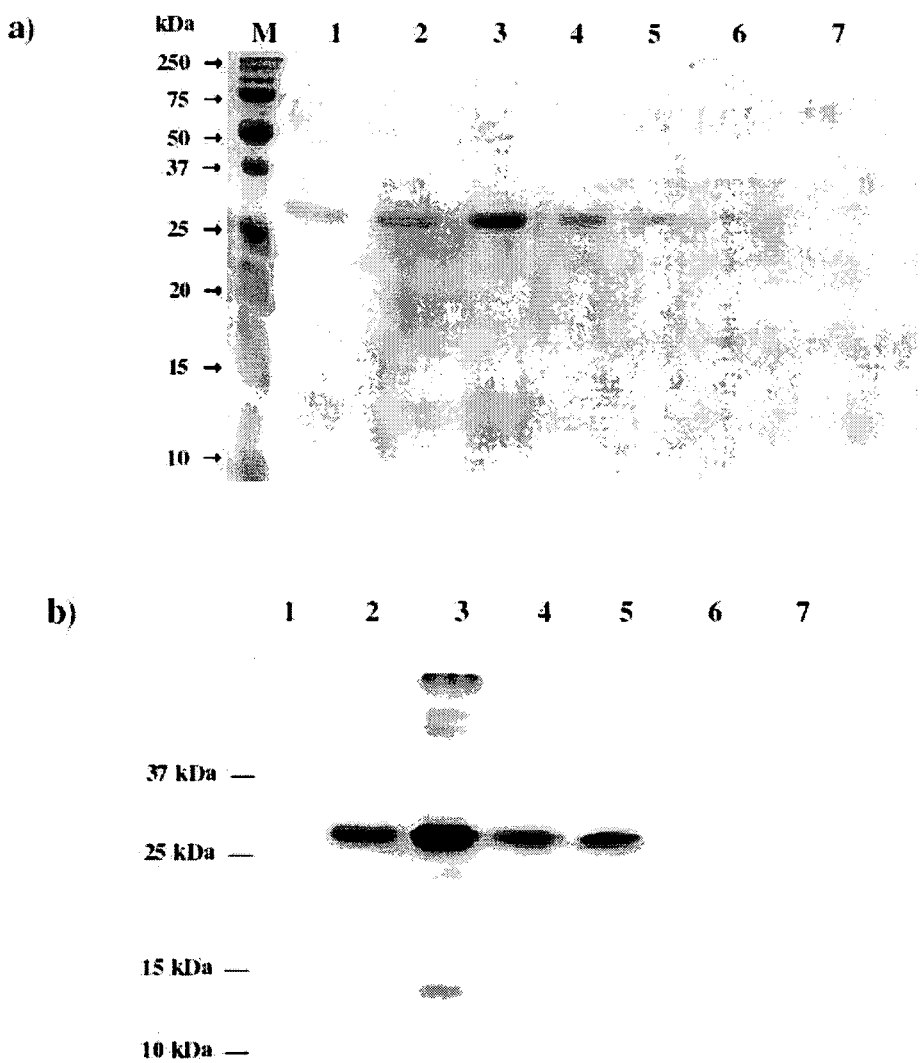
FIGS. 7a and 7b show analysis of Lys87 samples eluted after purification on the AKTA FPLC system using Coomassie blue staining (a) and Western Blot (b).

In order to improve the purity of the Lys87 obtained after the initial purification and solublization process, Lys 87 was further purified using AKTA FPLC chromatography system. The samples eluted during the purification process indicated a reduced number of undesired proteins and an increased amount of lysin (FIGS. 7a and 7b).

Example 3

Analysis of Lytic Activity of Lys87

Both the impure Lys87 isolated from the inclusion bodies and the Lys87 purified using the AKTA FPLC system were tested for lytic activity in several clinical isolates of gram-positive bacteria. The assay was carried out according to the protocol described in the Experimental Methods section. Table II shows that the Lys87 isolated from the inclusion bodies inhibited growth in all of the gram-positive bacteria tested except *Streptococcus* sp. As expected the lysin did not exhibit lytic activity against the gram-negative bacteria *E. coli*. Table III verifies that the purified Lys87 isolated using the AKTA FPLC system has the same range of lytic activity of the impure Lys87 isolated from inclusion bodies using a subset of the isolates of Table II.

TABLE II

Lytic Action of Lys87 isolated from Inclusion Bodies

| No. Ð | Species Ð | Lytic Activity Ð |
|---|---|---|
| 1 | *Staphylococcus aureus* Ð | +++ |
| 2 | *Staphylococcus aureus* Ð | + |
| 3 | *Staphylococcus aureus* Ð | +++ |
| 4 | *Staphylococcus aureus* Ð | ++ |
| 5 | *Staphylococcus aureus* Ð | + |
| 6 | *Staphylococcus aureus* Ð | +++ |
| 7 | *Staphylococcus aureus* Ð | ++ |
| 8 | *Staphylococcus aureus* Ð | + |
| 9 | *Staphylococcus aureus* Ð | ++ |
| 10 | *Staphylococcus aureus* Ð | ++ |
| 11 | *Staphylococcus aureus* Ð | ++ |
| 12 | *Staphylococcus aureus* Ð | + |
| 13 | *Staphylococcus aureus* Ð | +++ |
| 14 | *Staphylococcus aureus* Ð | ++ |
| 15 | *Staphylococcus aureus* Ð | +++ |
| 16 | *Staphylococcus aureus* Ð | ++ |
| 17 | *Staphylococcus aureus* Ð | + |
| 18 | *Staphylococcus aureus* Ð | ++ |
| 19 | *Staphylococcus aureus* Ð | +++ Ð |
| 20 | *Staphylococcus aureus* Ð | ++ |
| 21 | *Staphylococcus aureus* Ð | +++ |
| 22 | *Staphylococcus aureus* Ð | + |
| 23 | *Staphylococcus aureus* Ð | +++ |
| 24 | *Staphylococcus aureus* Ð | +++ |
| 25 | *Staphylococcus aureus* Ð | +++ |
| 26 | *Staphylococcus aureus* Ð | + |
| 27 | *Staphylococcus aureus* Ð | ++ |
| 28 | *Staphylococcus aureus* Ð | + |
| 29 | *Staphylococcus aureus* Ð | ++ |
| 30 | *Staphylococcus aureus* Ð | + |
| 31 | *Staphylococcus aureus* Ð | +++ |
| 32 | *Staphylococcus aureus* Ð | ++ |
| 33 | *Staphylococcus aureus* Ð | ++ |
| 34 | *Staphylococcus aureus* Ð | ++ |
| 35 | *Staphylococcus aureus* Ð | ++ |
| 36 | *Staphylococcus aureus* Ð | +++ |
| 37 | *Staphylococcus aureus* Ð | +++ |
| 38 | *Staphylococcus aureus* Ð | + |
| 39 | *Staphylococcus aureus* Ð | + |
| 40 | *Staphylococcus aureus* Ð | +++ |
| 41 | *Staphylococcus aureus* Ð | + |
| 42 | *Staphylococcus aureus* Ð | ++ |
| 43 | *Staphylococcus aureus* Ð | ++ |
| 44 | *Staphylococcus aureus* Ð | ++ |
| 45 | *Staphylococcus aureus* Ð | ++ |
| 46 | *Staphylococcus aureus* Ð | +++ |
| 47 | *Staphylococcus aureus* Ð | ++ |
| 48 | *Staphylococcus aureus* Ð | +++ |
| 49 | *Staphylococcus aureus* Ð | ++ |
| 50 | *Staphylococcus aureus* Ð | +++ |
| 51 | *Staphylococcus aureus* Ð | + |
| 52 | *Staphylococcus aureus* Ð | ++ |
| 53 | *Staphylococcus aureus* Ð | + |
| 54 | *Staphylococcus aureus* Ð | ++ |
| 55 | *Staphylococcus aureus* Ð | ++ |
| 56 | *Staphylococcus aureus* Ð | ++ |
| 57 | *Staphylococcus aureus* Ð | + |
| 58 | *Staphylococcus aureus* Ð | + |
| 59 | *Staphylococcus aureus* Ð | ++ |
| 60 | *Staphylococcus aureus* Ð | + |
| 61 | *Staphylococcus aureus* Ð | + |
| 62 | *Staphylococcus aureus* Ð | +++ |
| 63 | *Staphylococcus aureus* Ð | ++ |
| 64 | *Staphylococcus aureus* Ð | +++ |
| 65 | *Staphylococcus aureus* Ð | ++ |
| 66 | *Staphylococcus aureus* Ð | +++ |
| 67 | *Staphylococcus aureus* Ð | ++ |
| 68 | *Staphylococcus aureus* Ð | ++ |

TABLE II-continued

Lytic Action of Lys87 isolated from Inclusion Bodies

| No. | Species | Lytic Activity |
|---|---|---|
| 69 | Staphylococcus aureus | +++ |
| 70 | Staphylococcus aureus | + |
| 71 | Staphylococcus aureus | +++ |
| 72 | Staphylococcus aureus | + |
| 73 | Staphylococcus aureus | ++ |
| 74 | Staphylococcus aureus | ++ |
| 75 | Staphylococcus aureus | +++ |
| 76 | Staphylococcus aureus | +++ |
| 77 | Staphylococcus aureus | +++ |
| 78 | Staphylococcus aureus | ++ |
| 79 | Staphylococcus epidermidis | + |
| 80 | Staphylococcus epidermidis | + |
| 81 | Staphylococcus epidermidis | + |
| 82 | Staphylococcus epidermidis | + |
| 83 | Staphylococcus epidermidis | ++ |
| 84 | Staphylococcus epidermidis | ++ |
| 85 | Staphylococcus auricularis | ++ |
| 86 | Staphylococcus capitis | + |
| 87 | Staphylococcus capitis | + |
| 88 | Staphylococcus capitis | + |
| 89 | Staphylococcus haemolyticus | + |
| 90 | Staphylococcus haemolyticus | + |
| 91 | Staphylococcus haemolyticus | + |
| 92 | Staphylococcus hominis | +++ |
| 93 | Staphylococcus hominis | +++ |
| 94 | Staphylococcus saprophyticus | ++ |
| 95 | Staphylococcus saprophyticus | ++ |
| 96 | Staphylococcus saprophyticus | ++ |
| 97 | Staphylococcus simulans | ++ |
| 98 | Staphylococcus xylosis | ++ |
| 99 | Micrococcus luteus | +++ |
| 100 | Bacillus subtilis | ++ |
| 101 | Bacillus pumilus | ++ |
| 102 | E. coli | − |
| 103 | Enterococcus faecalis | + |
| 104 | Enterococcus sp. | + |
| 105 | Enterococcus hirae | + |
| 106 | Enterococcus faecium | + |
| 107 | Enterococcus avium | + |
| 108 | Streptococcus pneumonia | − |
| 109 | Streptococcus A | − |
| 110 | Streptococcus B | − |

+++ = strong lytic activity,
++ = medium lytic activity,
+ light lytic activity,
− = no lytic activity

TABLE III

Lytic activity of FPLC purified Lys87

| No. | Species | Lytic Activity |
|---|---|---|
| 75 | Staphylococcus aureus | ++ |
| 76 | Staphylococcus aureus | +++ |
| 77 | Staphylococcus aureus | +++ |
| 78 | Staphylococcus aureus | ++ |
| 83 | Staphylococcus epidermidis | + |
| 85 | Staphylococcus auricularis | ++ |
| 88 | Staphylococcus capitis | + |
| 91 | Staphylococcus haemolyticus | ++ |
| 92 | Staphylococcus hominis | +++ |
| 94 | Staphylococcus saprophyticus | ++ |
| 97 | Staphylococcus simians | ++ |
| 98 | Staphylococcus xylosis | ++ |
| 99 | Micrococcus luteus | +++ |
| 100 | Bacillus subtilis | ++ |
| 101 | Bacillus pumilus | +++ |
| 102 | E. coli | − |
| 103 | Enterococcus faecalis | ++ |
| 104 | Enterococcus sp. | + |
| 105 | Enterococcus hirae | +++ |
| 106 | Enterococcus faecium | + |
| 107 | Enterococcus avium | + |
| 108 | Streptococcus pneumonia | − |
| 109 | Streptococcus A | − |
| 110 | Streptococcus B | − |

+++ = strong lytic activity,
++ = medium lytic activity,
+ light lytic activity,
− = no lytic activity Example 4

Determination of MIC of Lys87 for S. aureus

Isolate 77 was used to determine the minimum inhibitory concentration (MIC) of Lys87 in S. aureus. The assay was carried out according to the protocol described in the Experimental Methods section. The MIC of Lys87 for S. aureus was determined to be 30 mg/ml.

Example 5

Lytic Activity of Lys87 in Liquid Culture

Evaluation of the lytic activity of Lys87 in liquid media was carried out according to the methods described above. A concentration of 50 mg/ml of purified Lys87 was found to be sufficient to inhibit the growth of S. aureus in liquid culture. The results are shown in Table IV.

TABLE IV

| Time (min) | S. aureus + Lys87 (OD600) | S. aureus + sample buffer (OD600) | S. aureus (OD600) |
|---|---|---|---|
| 0 | 0.967 | 0.932 | 1.190 |
| 5 | 0.965 | 0.960 | 1.205 |
| 10 | 0.970 | 0.983 | 1.220 |
| 15 | 0.970 | 0.995 | 1.240 |
| 20 | 0.963 | 1.026 | 1.280 |
| 25 | 0.950 | 1.080 | 1.330 |
| 30 | 0.930 | 1.116 | 1.378 |
| 35 | 0.910 | 1.163 | 1.412 |
| 40 | 0.910 | 1.202 | 1.450 |
| 45 | 0.897 | 1.240 | 1.472 |
| 50 | 0.896 | 1.271 | 1.486 |
| 55 | 0.879 | 1.307 | 1.515 |
| 60 | 0.845 | 1.338 | 1.536 |
| 70 | 0.869 | 1.373 | 1.572 |
| 80 | 0.851 | 1.394 | 1.600 |
| 100 | 0.816 | 1.417 | 1.618 |
| 120 | 0.809 | 1.479 | 1.620 |

Example 6

Construction of Chimeric Genes

The chimeric endolysin genes lys170-87 and lys168-87 were constructed to carry the coding sequences for the CD domains of Lys170 or Lys 168, respectively, fused to the cell wall binding domain (CWBD)-encoding sequence of lys87. The technique of Overlap-Extension by Polymerase Chain Reaction (OE-PCR) was used. See, e.g., Ho, S. N., Hunt, H.

D., Horton, R. M., Pullen, J. K., and Pease, L. R. (1989). Site-directed mutagenesis by overlap extension using the polymerase chain reaction. Gene. 77: 51-59. FIGS. 9 and 10 depict the details of the nucleotide sequence of the chimeric genes and of the primary sequence of resulting products. Specifically, FIGS. 9a and 9b show the nucleic acid sequence (SEQ ID NO:3) and its encoded amino acid sequence (SEQ ID NO:4), respectively, of the chimeric construct lysin170-87. Sequences deriving from gene lys170 are in bold: sequences from gene lys87 are in plain text; vector born sequences are in italics. Similarly, FIGS. 10a and 10b show the nucleic acid sequence (SEQ ID NO:5) and its encoded amino acid sequence (SEQ ID NO:6), respectively, of the chimeric construct lysin168-87. Sequences deriving from gene lys168 are in bold; sequences from gene lys87 are in plain text; vector born sequences are in italics.

Example 7

Expression and Purification of Lys170-87 and Lys168-87

The chimeric genes lys170-87 and lys168-87 were cloned in the expression vector pIVEX2.3d (Roche Applied Science), under the control of the inducible promoter $P_{T7}$, giving rise to recombinant plasmids pSF170-87 and pSF168-87, respectively. The chimeric endolysins produced from these constructs display a vector-encoded, C-terminal extension of 11 amino acid residues (PGGGSHHHHHH), which constitute a linker region and hexahistidine tail employed for immuno-detection and affinity purification of the enzymes (FIGS. 9 and 10).

These constructs were used to transform the expression strain CG61 (Sao-José, C., Parreira, R., Vieira, G. and Santos, M. A. (2000). The N-terminal region of the Oenococcus oeni bacteriophage fOg44 lysin behaves as a bona fide signal peptide in *Escherichia coli* and as a cis-inhibitory element, preventing lytic activity on oenococcal cells. J. Bacteriol. 182: 5823-5831), which carries plasmid pGP1-2 and that provides a source of T7 RNA polymerase upon thermal induction. The resulting strains (SF170-87 and SF168-87) where grown in LB medium supplemented with 100 µg/ml of ampicillin and 30 µg/ml kanamycin until the cultures optical density at 600 nm ($OD_{600}$) reached 0.8-1.0. At this point cultures were thermoinduced (42° C., 30 min, with agitation) and then left to incubate for 14 hours at 16° C.

Cells were recovered by centrifugation and suspended in 1/50 volume of lysis buffer A (20 mM Heppes pH 6.5, 500 mM NaCl, 1% glycerol, 1 mM DTT and 20 mM imidazole). Cells were disrupted upon sonication and the soluble fraction filtered through 0.22 µm before its application in a HisTrap™ HP (GE Healthcare) column coupled to FPLC system (AKTA, GE Heathcare). The column was washed first with 10-15 column volumes of lysis buffer A and then with the same volume of lysis buffer B (same composition as buffer A except that the imidazole was at a concentration of 50 mM). The column-bound proteins were eluted in a single step with an elution buffer again having the same composition as buffer A except that imidazole was at a concentration of 500 mM. The fractions containing the pure enzymes were pooled, concentrated, and changed to the enzyme storage buffer (50 mM Pho-Na pH 6.5, 500 mM NaCl, 25% glycerol. 1 mM DTT) using a HiTrap™ Desalting column (GE Healthcare). Preparations of pure chimeric endolysins were maintained at −20° C. until use.

Figure 11:
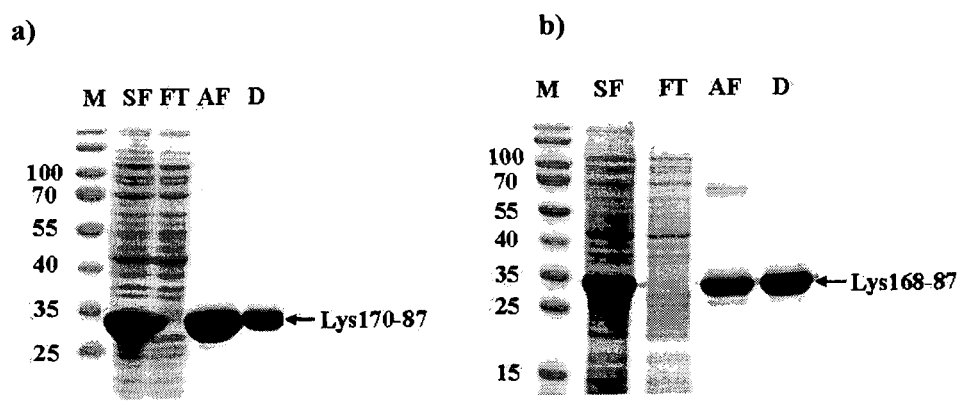
FIGS. 11a and 11b shows SDS-PAGE analysis of the purification process of Lys 170-87 (a) and Lys 168-87 (b). M stands for Molecular weight marker; SF, total soluble fraction; FT, affinity column flowthrough; AF, fraction corresponding to the affinity peak; D, desalted enzyme preparation.

The methodology described above allowed the production of high amounts of the chimeric enzymes in their soluble form. After the purification protocol, high yields of the enzymes in a highly pure state were obtained (FIGS. 11a and 11b).

Example 8

Analysis of Lys170-87 and Lys168-87 Lytic Activity

To study the lytic activity of the chimeric endolysins different quantities of the pure enzymes (10, 5, 1, and 0.2 µg), in a 5 µl volume, where spotted on the surface of a soft agar medium containing viable target bacteria (a total of 123 strains was tested). The different target bacteria were grown in appropriate media until $OD_{600}$=0.8-1.0 and concentrated 100-fold in fresh media. One hundred microliters of this cell suspension was incorporated in 10 ml of soft-agar medium (25 mM Phosphate-Na buffer pH 6.5, 250 mM NaCl, 0.7% agar) and poured in a Petri dish. This procedure guaranteed a homogeneous and dense lawn of target bacteria. The relative lytic activity obtained with the various enzyme amounts was qualitatively evaluated by registering the dimensions and transparency of lysis halos, after overnight incubation at 37° C.

The bacterial strains tested were: 101 strains of *S. aureus* (of which 39% were MRSA). 5 of *S. epidermidis*, 3 of *S. haemolyticos*, 3 of *S. saprophyticus*, 4 of *Enterococcus* spp., I of *Micrococcus luteus*, 2 of *Streptococcus pyogenes*, 1 of *Bacillus subtilis*, 1 of *Bacillus licheniformis* and 2 of *E. coli*. These bacterial strains were isolated during years 2005 to 2009 from clinical samples (including blood, urine, skin lesions and medical devices) in different Portuguese hospital and clinical settings, except for the *Micrococcus* and *Bacillus* strains (ATCC strains).

Lytic activity of Lys170-87 and Lys168-87 against *S. aureus* strain 566/07 was also evaluated in a liquid medium (25 mM Phosphate-Na buffer pH 6.5, 250 mM NaCl). Cultures of the *S. aureus* strain 566/07 were grown until exponential growth phase ($OD_{600}$=0.3-0.4), recovered by centrifugation and concentrated 2-fold in the liquid medium. Ten micrograms of each purified enzyme (in a 5 µl volume) were then added to one nil of this cell suspension and cell lysis was monitored by registering $OD_{600}$ values at different time points after endolysin addition. One milliliter of the cell suspension added of 5 µl of enzyme storage buffer served as negative control.

Figure 12:
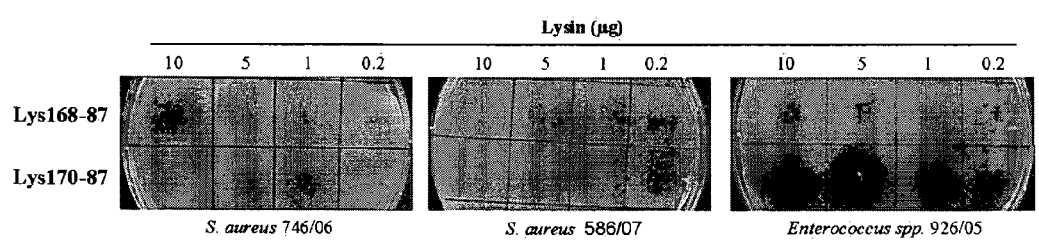
FIG. 12 shows three examples illustrating the results obtained for Lys168-87 and Lys170-87 when assayed for their activity on lawns of target bacteria.

The ability of the chimeric enzymes to lyse viable bacteria incorporated in a soft-agar medium was evaluated as described above. Briefly, different amounts of the enzymes were spotted on a dense lawn of viable, target bacteria (123 bacterial strains tested) and lytic activity was monitored by the appearance of lysis halos after overnight incubation at 37° C. FIG. 12 presents a few examples of the results obtained.

The results showed that the chimeric lysins were able to lyse strains of all the tested bacterial species, except of the Gram-negative species *E. coli*, as expected (Tables V and VI). Table V depicts the relative activity of Lys168-87 and Lys170-87 in 123 bacterial strains.

TABLE V

| Strain ID | Bacterial species | Lytic activity a) | | | | | | | |
|---|---|---|---|---|---|---|---|---|---|
| | | Lys168-87 | | | | Lys170-87 | | | |
| | Lysin amount (μg) | 10 | 5 | 1 | 0.2 | 10 | 5 | 1 | 0.2 |
| 919/05 | *Staphylococcus aureus* | +++ | ++ | + | +/− | ++ | + | + | +/− |
| 964/05 | *Staphylococcus aureus* | +++ | +++ | + | + | +++ | ++ | + | +/− |
| 1011/05 | *Staphylococcus aureus* (MRSA) | +++ | ++ | + | +/− | ++ | + | + | +/− |
| 1013/05 | *Staphylococcus aureus* | +++ | ++ | + | +/− | + | + | +/− | +/− |
| 1018/05 | *Staphylococcus aureus* (MRSA) | +++ | +++ | ++ | + | +++ | ++ | ++ | + |
| 1133/05 | *Staphylococcus aureus* | ++ | + | − | − | + | +/− | − | − |
| 1152/05 | *Staphylococcus aureus* | +++ | +++ | − | − | ++ | + | − | − |
| 1154/05 | *Staphylococcus aureus* | ++ | + | − | − | + | +/− | − | − |
| 1275/05 | *Staphylococcus aureus* (MRSA) | +++ | + | + | − | ++ | + | − | − |
| 1319/05 | *Staphylococcus aureus* | ++ | +/− | − | − | +/− | − | − | − |
| 1390/05 | *Staphylococcus aureus* | +++ | +++ | ++ | + | ++ | + | +/− | − |
| 1463/05 | *Staphylococcus aureus* (MRSA) | ++ | + | +/− | − | ++ | + | +/− | − |
| 1538/05 | *Staphylococcus aureus* | +++ | + | +/− | − | ++ | + | − | − |
| 1623/05 | *Staphylococcus aureus* | ++ | + | − | − | + | − | − | − |
| 1627/05 | *Staphylococcus aureus* | ++ | + | − | − | + | − | − | − |
| 1641/05 | *Staphylococcus aureus* (MRSA) | ++ | + | − | − | + | − | − | − |
| 1644/05 | *Staphylococcus aureus* (MRSA) | + | + | +/− | − | +/− | +/− | − | − |
| 1745/05 | *Staphylococcus aureus* | ++ | − | − | − | + | − | − | − |
| 1862/05 | *Staphylococcus aureus* (MRSA) | +++ | ++ | +/− | − | ++ | +/− | − | − |
| 1872/05 | *Staphylococcus aureus* | +++ | ++ | +/− | − | − | − | − | − |
| 1976/05 | *Staphylococcus aureus* | ++ | + | − | − | +/− | − | − | − |
| 2121/05 | *Staphylococcus aureus* (MRSA) | − | − | − | − | +/− | − | − | − |
| 124/06 | *Staphylococcus aureus* (MRSA) | +++ | ++ | + | − | + | + | +/− | − |
| 351/06 | *Staphylococcus aureus* | +++ | ++ | + | − | + | +/− | − | − |
| 399/06 | *Staphylococcus aureus* | +++ | +++ | +/− | +/− | + | +/− | − | − |
| 400/06 | *Staphylococcus aureus* | +/− | +/− | +/− | − | − | − | − | − |
| 623/06 | *Staphylococcus aureus* (MRSA) | + | − | − | − | +/− | − | − | − |
| 644/06 | *Staphylococcus aureus* (MRSA) | +++ | +++ | + | +/− | + | + | +/− | +/− |
| 746/06 | *Staphylococcus aureus* (MRSA) | +++ | ++ | ++ | +/− | + | +/− | − | − |
| 748/06 | *Staphylococcus aureus* | + | + | +/− | − | + | + | − | − |

TABLE V-continued

| Strain ID | Bacterial species | Lytic activity a) | | | | | | | |
|---|---|---|---|---|---|---|---|---|---|
| 815/06 | Staphylococcus aureus (MRSA) | +++ | +++ | + | +/− | ++ | + | + | + |
| 920/06 | Staphylococcus aureus | +++ | +++ | ++ | + | + | + | +/− | − |
| 1035/06 | Staphylococcus aureus (MRSA) | +++ | +++ | ++ | + | ++ | ++ | + | + |
| 1037/06 | Staphylococcus aureus (MRSA) | +++ | ++ | + | + | +++ | ++ | + | +/− |
| 1038/06 | Staphylococcus aureus | +++ | ++ | + | +/− | + | +/− | − | − |
| 1039/06 | Staphylococcus aureus | +++ | ++ | ++ | + | ++ | + | +/− | − |
| 1076/06 | Staphylococcus aureus (MRSA) | +++ | +++ | ++ | ++ | ++ | ++ | + | +/− |
| 1077/06 | Staphylococcus aureus (MRSA) | +++ | ++ | ++ | + | + | + | +/− | − |
| 1102/06 | Staphylococcus aureus (MRSA) | +++ | ++ | + | +/− | ++ | + | +/− | − |
| 1149/06 | Staphylococcus aureus (MRSA) | +++ | +++ | ++ | + | ++ | + | +/− | − |
| 1156/06 | Staphylococcus aureus | +++ | +++ | ++ | + | + | +/− | − | − |
| 1157/06 | Staphylococcus aureus (MRSA) | +++ | +++ | +++ | +/− | ++ | ++ | ++ | +/− |
| 1159/06 | Staphylococcus aureus | ++ | ++ | + | + | + | + | +/− | +/− |
| 1201/06 | Staphylococcus aureus (MRSA) | +++ | ++ | ++ | +/− | + | + | +/− | − |
| 1203/06 | Staphylococcus aureus | +++ | +++ | ++ | +/− | + | +/− | − | − |
| 1204/06 | Staphylococcus aureus (MRSA) | ++ | ++ | +/− | − | − | − | − | − |
| 1209/06 | Staphylococcus aureus | +++ | ++ | + | − | + | +/− | − | − |
| 84/07 | Staphylococcus aureus (MRSA) | +++ | +++ | ++ | + | ++ | ++ | + | +/− |
| 161/07 | Staphylococcus aureus (MRSA) | +++ | +++ | ++ | + | + | + | +/− | − |
| 86/07 | Staphylococcus aureus (MRSA) | +++ | ++ | + | +/− | + | +/− | − | − |
| 163/07 | Staphylococcus aureus (MRSA) | +++ | ++ | + | + | + | + | − | − |
| 166/07 | Staphylococcus aureus (MRSA) | + | + | +/− | − | + | + | − | − |
| 196/07 | Staphylococcus aureus | +++ | +++ | ++ | + | + | + | + | + |
| 214/07 | Staphylococcus aureus | ++ | ++ | + | +/− | + | +/− | − | − |
| 224/07 | Staphylococcus aureus | + | + | +/− | +/− | +/− | +/− | − | − |
| 400/07 | Staphylococcus aureus (MRSA) | +++ | +++ | ++ | + | + | + | +/− | − |
| 463/07 | Staphylococcus aureus | +++ | ++ | + | +/− | + | + | +/− | − |
| 464/07 | Staphylococcus aureus | +++ | ++ | + | − | + | +/− | − | − |
| 545/07 | Staphylococcus aureus | +++ | +++ | ++ | + | ++ | + | + | + |
| 547/07 | Staphylococcus aureus | +++ | +++ | ++ | +/− | ++ | ++ | + | − |

TABLE V-continued

| Strain ID | Bacterial species | Lytic activity a) | | | | | | | |
|---|---|---|---|---|---|---|---|---|---|
| 565/07 | Staphylococcus aureus | ++ | ++ | +/− | − | + | +/− | − | − |
| 566/07 | Staphylococcus aureus | +++ | +++ | +++ | + | +++ | ++ | + | +/− |
| 567/07 | Staphylococcus aureus | +++ | +++ | ++ | + | + | + | + | +/− |
| 662/07 | Staphylococcus aureus | ++ | ++ | + | +/− | + | +/− | +/− | − |
| 171/07 | Staphylococcus aureus | +++ | ++ | + | +/− | + | +/− | − | − |
| 223/07 | Staphylococcus aureus | ++ | ++ | + | +/− | +/− | − | − | − |
| 546/07 | Staphylococcus aureus | +++ | ++ | + | +/− | + | + | + | +/− |
| 578/07 | Staphylococcus aureus | +++ | +++ | ++ | − | + | + | + | − |
| 586/07 | Staphylococcus aureus | +++ | +++ | ++ | + | +++ | ++ | ++ | + |
| 594/07 | Staphylococcus aureus | − | − | − | − | − | − | − | − |
| 663/07 | Staphylococcus aureus | +++ | +++ | ++ | − | ++ | ++ | + | − |
| 322/07 | Staphylococcus aureus (MRSA) | + | + | + | − | +/− | +/− | +/− | − |
| 325/07 | Staphylococcus aureus | +++ | +++ | ++ | +/− | ++ | ++ | + | +/− |
| 743/06 | Staphylococcus aureus | +++ | +++ | ++ | + | + | + | + | +/− |
| 162/07 | Staphylococcus aureus (MRSA) | +++ | +++ | ++ | + | + | + | + | + |
| 465/07 | Staphylococcus aureus (MRSA) | +++ | ++ | + | − | ++ | ++ | + | − |
| 466/07 | Staphylococcus aureus | +++ | ++ | + | +/− | ++ | + | + | − |
| 590/07 | Staphylococcus aureus (MRSA) | +++ | +++ | ++ | +/− | ++ | ++ | + | +/− |
| 53/08 | Staphylococcus aureus | +++ | +++ | ++ | +/− | ++ | ++ | + | + |
| 55/08 | Staphylococcus aureus | +++ | +++ | ++ | +/− | + | + | +/− | +/− |
| 56/08 | Staphylococcus aureus | ++ | ++ | + | +/− | + | +/− | − | − |
| 97/08 | Staphylococcus aureus (MRSA) | +++ | +++ | ++ | − | ++ | + | + | +/− |
| 129/08 | Staphylococcus aureus | +++ | +++ | +++ | ++ | + | + | + | + |
| 130/08 | Staphylococcus aureus | ++ | ++ | +/− | − | + | + | + | +/− |
| 1020/05 | Staphylococcus aureus | +++ | ++ | + | + | +++ | ++ | + | + |
| 941/05 | Staphylococcus aureus | ++ | + | +/− | − | +/− | − | − | − |
| 965/05 | Staphylococcus aureus (MRSA) | +++ | ++ | + | − | +/− | − | − | − |
| 1094/05 | Staphylococcus aureus | +++ | +++ | ++ | ++ | ++ | ++ | + | − |
| 2013/05 | Staphylococcus aureus (MRSA) | +++ | + | +/− | − | + | − | − | − |
| 793/06 | Staphylococcus aureus | ++ | ++ | + | +/− | +/− | − | − | − |
| 862/06 | Staphylococcus aureus (MRSA) | − | − | − | − | − | − | − | − |
| 455/05 | Staphylococcus aureus | − | − | − | − | − | − | − | − |
| 755/05 | Staphylococcus aureus | +++ | +++ | ++ | + | ++ | + | +/− | − |
| 1389/05 | Staphylococcus aureus | +++ | ++ | + | − | ++ | − | − | − |
| 1649/05 | Staphylococcus | +++ | ++ | + | +/− | ++ | + | +/− | − |

TABLE V-continued

| Strain ID | Bacterial species | Lytic activity a) | Đ | Đ | Đ | Đ | Đ | Đ | Đ |
|---|---|---|---|---|---|---|---|---|---|
| 2030/05 | Staphylococcus aureus Đ | ++ | + | – | – | +/– | – | – | – |
| 2144/05 | Staphylococcus aureus (MRSA) | +++ | ++ | + | +/– | + | +/– | – | – |
| 541/06 Đ | Staphylococcus aureus Đ | +++ | +++ | ++ | +/– | +/– | – | – | – |
| 1007/06 | Staphylococcus aureus Đ | ++ | + | +/– | – | + | +/– | – | – |
| 1211/06 | Staphylococcus aureus (MRSA) | +++ | +++ | +++ | ++ | + | + | + | +/– |
| 1736/05 | Staphylococcus aureus (MRSA) | ++ | + | – | – | + | +/– | – | – |
| 107/08 Đ | Staphylococcus epidermidis Đ | +++ | ++ | + | +/– | – | – | – | – |
| 114/08 Đ | Staphylococcus epidermidis Đ | ++ | ++ | + | – | +/– | – | – | – |
| 546/06 Đ | Staphylococcus epidermidis Đ | +++ | ++ | + | +/– | ++ | ++ | +/– | – |
| 158/08 Đ | Staphylococcus epidermidis Đ | +++ | +++ | ++ | + | + | + | – | – |
| 1930/05 | Staphylococcus haemolyticus Đ | ++ | ++ | + | + | ++ | + | + | + |
| 05/06 | Staphylococcus haemolyticus Đ | +++ | ++ | ++ | + | + | + | + | +/– |
| 06/06 | Staphylococcus haemolyticus Đ | +++ | ++ | + | + | ++ | ++ | + | + |
| 1908/05 | Staphylococcus saprophyticus Đ | – | – | – | – | – | – | – | – |
| 1909/05 | Staphylococcus saprophyticus Đ | ++ | ++ | + | + | + | ++ | + | – |
| 110/08 Đ | Staphylococcus saprophyticus Đ | ++ | ++ | + | + | ++ | ++ | + | + |
| 1518/05b) | Enterococcus sp.Đ | +/– | +/– | – | – | ++ | + | +/– | – |
| 926/05c) | Enterococcus sp. Đ | ++ | ++ | + | +/– | +++ | +++ | ++ | + |
| 46/06 | Enterococcus faecalis Đ | ++ | ++ | + | +/– | +++ | +++ | ++ | + |
| 188/06 Đ | Enterococcus faecium Đ | +/– | – | – | – | ++ | + | +/– | – |
| 12/08 | Streptococcus pyogenes Đ | + | + | +/– | – | ++ | ++ | + | – |
| 13/08 | Streptococcus pyogenes Đ | ++ | + | – | – | + | +/– | – | – |
| 575/07 Đ | Micrococcus luteus Đ | + | + | + | +/– | + | + | +/– | +/– |
| 01/09 | Bacillus licheni formes Đ | +++ | +++ | ++ | – | +++ | +++ | +++ | ++ |
| 02/09 | Bacillus subtilis Đ | +++ | ++ | ++ | + | + | + | ++ | + |
| 35/08 | Escherichia coli Đ | – | – | – | – | – | – | – | – |
| 44/08 | Escherichia coli Đ | – | – | – | – | – | – | – | – |

Figure 13:
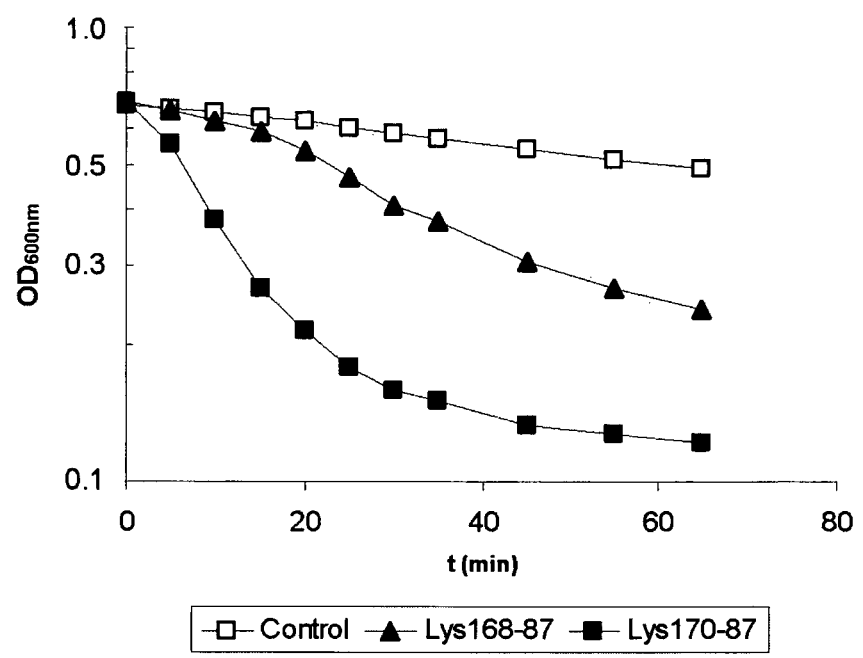
FIG. 13 shows lytic activity of Lys168-87 and Lys 170-87 on cells of *S. aureus* strain 566/07 suspended in a liquid medium (25 mM Phosphate-Na buffer pH 6.5, 250 mM NaCl). Each enzyme was added at 10 µg/ml concentration. The control is a cell suspension added of enzyme storage buffer. The presented data correspond to the average of three independent experiments.

In Table V,

'Lytic activity a)' indicates the sensitivity of each strain to the lytic action of the chimeric enzymes, which was evaluated based on a relative scale ranging from turbid/small (+/–) to clear/large (+++) lysis halos; resistance to lytic action is indicated as (–).
1518/05b) represents the host strain of phage F168/08; and
926/05c) represents the host strain of phage F170/08.
Notably, of the 40 MRSA strains tested only 1 (862/06) presented resistance to both enzymes (Table V). Interestingly, when the activity of both enzymes was tested against *S. aureus* strain 566/07 in a liquid medium, as described above, Lys170-87 showed a higher lytic efficiency when compared to Lys168-87 (FIG. 13), and in contrast to the results obtained in soft-agar medium (Table V).

Table VI below compares the lytic activity of Lys168-87 and Lys170-87.

TABLE VI

| Bacterial species (NO of strains) | Lytic Activity (%)a) | | | | | | | |
|---|---|---|---|---|---|---|---|---|
| | Lys168-87 (µg) | | | | Lys170-87 (µg) | | | |
| | 10 | 5 | 1 | 0.2 | 10 | 5 | 1 | 0.2 |
| S. aureus (101) | 96 | 94 | 85 | 59 | 94 | 78 | 44 | 30 |
| S. epidermidis (5) | 100 | 100 | 80 | 60 | 80 | 60 | 20 | 0 |
| S. haemolyticus (3) | 100 | 100 | 100 | 100 | 100 | 100 | 100 | 100 |
| S. saprophyticus (3) | 67 | 67 | 67 | 67 | 67 | 67 | 67 | 33 |
| Enterococcus spp. (4) | 100 | 75 | 50 | 50 | 100 | 100 | 100 | 50 |
| M. luteus (1) | 100 | 100 | 100 | 100 | 100 | 100 | 100 | 100 |
| Str pyogenes (2) | 100 | 100 | 50 | 0 | 100 | 100 | 50 | 0 |
| Bacillus spp. (2) | 100 | 100 | 100 | 50 | 100 | 100 | 100 | 100 |
| E. coli (2) | 0 | 0 | 0 | 0 | 0 | 0 | 0 | 0 |

Lytic Activity (%)a) shows the percentage of stains of each bacterial species that were sensitive to the lytic action of the different amounts of Lys168-87 and Lys170-87 tested.
Considering S. aureus strains, the major target for which Lys170-87 and Lys168-87 were designed, it was observed that more than 90% of the tested strains were sensitive to the lytic action of 10 µg of either lysin (Table VI).
In the described experimental conditions, and for the same amount of enzyme, Lys168-87 appeared to exhibit stronger lytic action against S. aureus when compared to Lys170-87 (Table VI).

Having described the invention with reference to particular compositions, method for detection, and source of activity, and proposals of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. It should be understood that any of the above described one or more elements from any embodiment can be combined with any one or more element in any other embodiment. Moreover, when a range is mentioned, it should be understood that it is contemplated that any real number that falls within the range is a contemplated end point. For example, if a range of 0.9 and 1.1 g/kg is given, it is contemplated that any real number value that falls within that range (for example, 0.954 to 1.052 g/kg) is contemplated as a subgenus range of the invention, even if those values are not explicitly mentioned. All references referred to herein are incorporated by reference in their entireties. Finally, the above description is not to be construed to limit the invention but the invention should rather be defined by the below claims.

The invention claimed is:

1. A chimeric polypeptide comprising the amino acid sequence of SEQ ID NO:4 or SEQ ID NO:6.

2. A pharmaceutical composition comprising the chimeric polypeptide of claim 1, and a pharmaceutically acceptable carrier.

* * * * *

SEQUENCE LISTING

<160> NUMBER OF SEQ ID NOS: 6

<210> SEQ ID NO 1
<211> LENGTH: 756
<212> TYPE: DNA
<213> ORGANISM: Bacteriophage 87
<220> FEATURE:
<221> NAME/KEY: CDS
<222> LOCATION: (1)..(756)

<400> SEQUENCE: 1

| atg aaa aca tac agt gaa gca aga gca agg tta cgt tgg tat caa ggt | 48 |
|---|---|
| Met Lys Thr Tyr Ser Glu Ala Arg Ala Arg Leu Arg Trp Tyr Gln Gly | |
| 1               5                  10                 15 | |

| aga tat att gat ttt gac ggt tgg tat ggt tac caa tgt gca gat tta | 96 |
|---|---|
| Arg Tyr Ile Asp Phe Asp Gly Trp Tyr Gly Tyr Gln Cys Ala Asp Leu | |
|              20                  25                 30 | |

| gca gtt gat tac att tat tgg ttg tta gaa att aga atg tgg gga aat | 144 |
|---|---|
| Ala Val Asp Tyr Ile Tyr Trp Leu Leu Glu Ile Arg Met Trp Gly Asn | |
|          35                  40                 45 | |

| gca aaa gat gca atc aat aac gat ttt aaa aac atg gca aca gta tat | 192 |
|---|---|
| Ala Lys Asp Ala Ile Asn Asn Asp Phe Lys Asn Met Ala Thr Val Tyr | |
| 50                  55                  60 | |

| gaa aac aca cca tcg ttt gtt cca caa ata ggt gat gtg gct gta ttt | 240 |
|---|---|
| Glu Asn Thr Pro Ser Phe Val Pro Gln Ile Gly Asp Val Ala Val Phe | |
| 65                  70                  75                  80 | |

| acc aaa gga ata tat aaa caa tac ggt cat att ggt tta gtg ttt aat | 288 |
|---|---|
| Thr Lys Gly Ile Tyr Lys Gln Tyr Gly His Ile Gly Leu Val Phe Asn | |
|              85                  90                 95 | |

| ggt ggt aat aca aac caa ttt tta att ttg gaa cag aac tat gac ggt | 336 |
|---|---|
| Gly Gly Asn Thr Asn Gln Phe Leu Ile Leu Glu Gln Asn Tyr Asp Gly | |
|          100                 105                110 | |

| aac gca aat acg cct gca aag tta cgt tgg gat aat tat tac ggc tgt | 384 |
|---|---|
| Asn Ala Asn Thr Pro Ala Lys Leu Arg Trp Asp Asn Tyr Tyr Gly Cys | |
|      115                 120                125 | |

| act cac ttt att aga cct aag tat aaa agt gag ggc tta atg aat aag | 432 |
|---|---|
| Thr His Phe Ile Arg Pro Lys Tyr Lys Ser Glu Gly Leu Met Asn Lys | |
|  130                 135                 140 | |

| atc aca aat aaa gtt aaa cca cct gct caa aaa gca gtc ggt aaa tct | 480 |
|---|---|
| Ile Thr Asn Lys Val Lys Pro Pro Ala Gln Lys Ala Val Gly Lys Ser | |
| 145                 150                 155                 160 | |

| gca agt aaa ata aca gtt gga agt aaa gcg cct tat aac ctt aaa tgg | 528 |
|---|---|
| Ala Ser Lys Ile Thr Val Gly Ser Lys Ala Pro Tyr Asn Leu Lys Trp | |
|              165                 170                175 | |

| tca aaa ggt gct tat ttt aat gcg aaa atc gac ggc tta ggt gct act | 576 |
|---|---|
| Ser Lys Gly Ala Tyr Phe Asn Ala Lys Ile Asp Gly Leu Gly Ala Thr | |
|          180                 185                190 | |

| tca gcc act aga tac ggt gat aat cgt act aac tat aga ttc gat gtt | 624 |
|---|---|
| Ser Ala Thr Arg Tyr Gly Asp Asn Arg Thr Asn Tyr Arg Phe Asp Val | |
|      195                 200                205 | |

| gga cag gct gta tac gcg cct gga aca tta ata tat gtg ttt gaa att | 672 |
|---|---|
| Gly Gln Ala Val Tyr Ala Pro Gly Thr Leu Ile Tyr Val Phe Glu Ile | |
|  210                 215                 220 | |

| ata gat ggt tgg tgt cgc att tat tgg aac aat cat aat gag tgg ata | 720 |
|---|---|
| Ile Asp Gly Trp Cys Arg Ile Tyr Trp Asn Asn His Asn Glu Trp Ile | |
| 225                 230                 235                 240 | |

| tgg cat gag aga ttg att gtg aaa gaa gtg ttt taa | 756 |
|---|---|
| Trp His Glu Arg Leu Ile Val Lys Glu Val Phe | |
|              245                 250 | |

```
<210> SEQ ID NO 2
<211> LENGTH: 251
<212> TYPE: PRT
<213> ORGANISM: Bacteriophage 87

<400> SEQUENCE: 2

Met Lys Thr Tyr Ser Glu Ala Arg Ala Arg Leu Arg Trp Tyr Gln Gly
1               5                   10                  15

Arg Tyr Ile Asp Phe Asp Gly Trp Tyr Gly Tyr Gln Cys Ala Asp Leu
            20                  25                  30

Ala Val Asp Tyr Ile Tyr Trp Leu Leu Glu Ile Arg Met Trp Gly Asn
        35                  40                  45

Ala Lys Asp Ala Ile Asn Asn Asp Phe Lys Asn Met Ala Thr Val Tyr
    50                  55                  60

Glu Asn Thr Pro Ser Phe Val Pro Gln Ile Gly Asp Val Ala Val Phe
65                  70                  75                  80

Thr Lys Gly Ile Tyr Lys Gln Tyr Gly His Ile Gly Leu Val Phe Asn
                85                  90                  95

Gly Gly Asn Thr Asn Gln Phe Leu Ile Leu Glu Gln Asn Tyr Asp Gly
            100                 105                 110

Asn Ala Asn Thr Pro Ala Lys Leu Arg Trp Asp Asn Tyr Gly Cys
        115                 120                 125

Thr His Phe Ile Arg Pro Lys Tyr Lys Ser Glu Gly Leu Met Asn Lys
    130                 135                 140

Ile Thr Asn Lys Val Lys Pro Pro Ala Gln Lys Ala Val Gly Lys Ser
145                 150                 155                 160

Ala Ser Lys Ile Thr Val Gly Ser Lys Ala Pro Tyr Asn Leu Lys Trp
                165                 170                 175

Ser Lys Gly Ala Tyr Phe Asn Ala Lys Ile Asp Gly Leu Gly Ala Thr
            180                 185                 190

Ser Ala Thr Arg Tyr Gly Asp Asn Arg Thr Asn Tyr Arg Phe Asp Val
        195                 200                 205

Gly Gln Ala Val Tyr Ala Pro Gly Thr Leu Ile Tyr Val Phe Glu Ile
    210                 215                 220

Ile Asp Gly Trp Cys Arg Ile Tyr Trp Asn Asn His Asn Glu Trp Ile
225                 230                 235                 240

Trp His Glu Arg Leu Ile Val Lys Glu Val Phe
                245                 250

<210> SEQ ID NO 3
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(894)

<400> SEQUENCE: 3 atg gca gga gaa gta ttt agt agc ttg att aca agt gta aat cct aac    48
Met Ala Gly Glu Val Phe Ser Ser Leu Ile Thr Ser Val Asn Pro Asn
1               5                   10                  15 cca atg aac gca ggt agc cgt aat ggt atc act atc gac acc att atc    96
Pro Met Asn Ala Gly Ser Arg Asn Gly Ile Thr Ile Asp Thr Ile Ile
            20                  25                  30 cta cat cac aat gca aca aca aat aaa gat gtt gct atg aac aca tgg   144
Leu His His Asn Ala Thr Thr Asn Lys Asp Val Ala Met Asn Thr Trp
        35                  40                  45
```

```
cta tta ggt ggt ggc gca ggt aca tct gct cat tat gaa tgt aca cca   192
Leu Leu Gly Gly Gly Ala Gly Thr Ser Ala His Tyr Glu Cys Thr Pro
     50                  55                  60 aca gaa att att gga tgt gtc ggt gag cag tat tca gca ttc cat gcc   240
Thr Glu Ile Ile Gly Cys Val Gly Glu Gln Tyr Ser Ala Phe His Ala
 65                  70                  75                  80 gga ggt aca ggt ggt ata gac gtt cct aag att gct aac cct aat caa   288
Gly Gly Thr Gly Gly Ile Asp Val Pro Lys Ile Ala Asn Pro Asn Gln
                 85                  90                  95 cgt tca ata ggt att gaa aat gta aac tcg tca gga gca cct aat tgg   336
Arg Ser Ile Gly Ile Glu Asn Val Asn Ser Ser Gly Ala Pro Asn Trp
            100                 105                 110 tct gta gac cct aga aca att aca aat tgt gct cgt tta gtg gca gat   384
Ser Val Asp Pro Arg Thr Ile Thr Asn Cys Ala Arg Leu Val Ala Asp
        115                 120                 125 att tgt aca cgt tat ggt att ccg tgt gac cga caa cat gtg tta gga   432
Ile Cys Thr Arg Tyr Gly Ile Pro Cys Asp Arg Gln His Val Leu Gly
    130                 135                 140 cat aac gaa gta act gca aca gca tgt ccc gga ggt atg gat gta gac   480
His Asn Glu Val Thr Ala Thr Ala Cys Pro Gly Gly Met Asp Val Asp
145                 150                 155                 160 gaa gtt gta cgt caa gct caa cag ttc atg gca gga ggc tct aac aat   528
Glu Val Val Arg Gln Ala Gln Gln Phe Met Ala Gly Gly Ser Asn Asn
                165                 170                 175 gca gtt aag ccg gag cca aaa gtt aaa cca cct gct caa aaa gca gtc   576
Ala Val Lys Pro Glu Pro Lys Val Lys Pro Pro Ala Gln Lys Ala Val
            180                 185                 190 ggt aaa tct gca agt aaa ata aca gtt gga agt aaa gcg cct tat aac   624
Gly Lys Ser Ala Ser Lys Ile Thr Val Gly Ser Lys Ala Pro Tyr Asn
        195                 200                 205 ctt aaa tgg tca aaa ggt gct tat ttt aat gcg aaa atc gac ggc tta   672
Leu Lys Trp Ser Lys Gly Ala Tyr Phe Asn Ala Lys Ile Asp Gly Leu
    210                 215                 220 ggt gct act tca gcc act aga tac ggt gat aat cgt act aac tat aga   720
Gly Ala Thr Ser Ala Thr Arg Tyr Gly Asp Asn Arg Thr Asn Tyr Arg
225                 230                 235                 240 ttc gat gtt gga cag gct gta tac gcg cct gga aca tta ata tat gtg   768
Phe Asp Val Gly Gln Ala Val Tyr Ala Pro Gly Thr Leu Ile Tyr Val
                245                 250                 255 ttt gaa att ata gat ggt tgg tgt cgc att tat tgg aac aat cat aat   816
Phe Glu Ile Ile Asp Gly Trp Cys Arg Ile Tyr Trp Asn Asn His Asn
            260                 265                 270 gag tgg ata tgg cat gag aga ttg att gtg aaa gaa gtg ttt ccc ggg   864
Glu Trp Ile Trp His Glu Arg Leu Ile Val Lys Glu Val Phe Pro Gly
        275                 280                 285 ggg ggt tct cat cat cat cat cat cat taa                           894
Gly Gly Ser His His His His His His
    290                 295

<210> SEQ ID NO 4
<211> LENGTH: 297
<212> TYPE: PRT
<213> ORGANISM: Artificial Sequence
<220> FEATURE:
<223> OTHER INFORMATION: Synthetic Construct

<400> SEQUENCE: 4

Met Ala Gly Glu Val Phe Ser Ser Leu Ile Thr Ser Val Asn Pro Asn
1               5                   10                  15

Pro Met Asn Ala Gly Ser Arg Asn Gly Ile Thr Ile Asp Thr Ile Ile
            20                  25                  30
```

-continued

```
Leu His His Asn Ala Thr Thr Asn Lys Asp Val Ala Met Asn Thr Trp
        35                  40                  45

Leu Leu Gly Gly Gly Ala Gly Thr Ser Ala His Tyr Glu Cys Thr Pro
    50                  55                  60

Thr Glu Ile Ile Gly Cys Val Gly Glu Gln Tyr Ser Ala Phe His Ala
65                  70                  75                  80

Gly Gly Thr Gly Gly Ile Asp Val Pro Lys Ile Ala Asn Pro Asn Gln
                85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
        115                 120                 125

Ile Cys Thr Arg Tyr Gly Ile Pro Cys Asp Arg Gln His Val Leu Gly
    130                 135                 140

His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Lys Val Lys Pro Ala Gln Lys Ala Val
            180                 185                 190

Gly Lys Ser Ala Ser Lys Ile Thr Val Gly Ser Lys Ala Pro Tyr Asn
        195                 200                 205

Leu Lys Trp Ser Lys Gly Ala Tyr Phe Asn Ala Lys Ile Asp Gly Leu
    210                 215                 220

Gly Ala Thr Ser Ala Thr Arg Tyr Gly Asp Asn Arg Thr Asn Tyr Arg
225                 230                 235                 240

Phe Asp Val Gly Gln Ala Val Tyr Ala Pro Gly Thr Leu Ile Tyr Val
                245                 250                 255

Phe Glu Ile Ile Asp Gly Trp Cys Arg Ile Tyr Trp Asn Asn His Asn
            260                 265                 270

Glu Trp Ile Trp His Glu Arg Leu Ile Val Lys Glu Val Phe Pro Gly
        275                 280                 285

Gly Gly Ser His His His His His His
    290                 295

<210> SEQ ID NO 5
<211> LENGTH: 828
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(828)

<400> SEQUENCE: 5 atg gtt aaa tta aat gat gta ctt agc tat gtc aac gga ctt gtc gga      48
Met Val Lys Leu Asn Asp Val Leu Ser Tyr Val Asn Gly Leu Val Gly
1               5                   10                  15 aaa ggc gtg gac gct gat gga tgg tat ggt act caa tgt atg gac ttg      96
Lys Gly Val Asp Ala Asp Gly Trp Tyr Gly Thr Gln Cys Met Asp Leu
            20                  25                  30 aca gta gac gtt atg caa cgc ttc ttc gga tgg cgc ccg tac ggt aat     144
Thr Val Asp Val Met Gln Arg Phe Phe Gly Trp Arg Pro Tyr Gly Asn
        35                  40                  45 gca att gcc ttg gtt gac cag cct atc cca gca ggc ttc caa aga atc     192
Ala Ile Ala Leu Val Asp Gln Pro Ile Pro Ala Gly Phe Gln Arg Ile
    50                  55                  60
```

```
cgt acc aca agc tct aca caa atc aaa gct ggt gac gtt atg ata tgg    240
Arg Thr Thr Ser Ser Thr Gln Ile Lys Ala Gly Asp Val Met Ile Trp
 65                  70                  75                  80 ggc tta gga tac tat gct caa tac ggt cac aca gga att gca acg gag    288
Gly Leu Gly Tyr Tyr Ala Gln Tyr Gly His Thr Gly Ile Ala Thr Glu
                 85                  90                  95 gat gga aga gct gac gga acc ttt gtc agt gtt gac caa aac tgg att    336
Asp Gly Arg Ala Asp Gly Thr Phe Val Ser Val Asp Gln Asn Trp Ile
            100                 105                 110 aac cca agc ctt gaa gta ggc agt cca gca gct gct atc cac cac aat    384
Asn Pro Ser Leu Glu Val Gly Ser Pro Ala Ala Ala Ile His His Asn
        115                 120                 125 atg gat ggt gtc tgg gga gtt atc cga cca cct tac gag gct gaa tca    432
Met Asp Gly Val Trp Gly Val Ile Arg Pro Pro Tyr Glu Ala Glu Ser
130                 135                 140 aag cct aaa cca cct gca cca aaa cca gat aaa cca aat cta gga caa    480
Lys Pro Lys Pro Pro Ala Pro Lys Pro Asp Lys Pro Asn Leu Gly Gln
145                 150                 155                 160 aaa gtt aaa cca cct gct caa aaa gca gtc ggt aaa tct gca agt aaa    528
Lys Val Lys Pro Pro Ala Gln Lys Ala Val Gly Lys Ser Ala Ser Lys
                165                 170                 175 ata aca gtt gga agt aaa gcg cct tat aac ctt aaa tgg tca aaa ggt    576
Ile Thr Val Gly Ser Lys Ala Pro Tyr Asn Leu Lys Trp Ser Lys Gly
            180                 185                 190 gct tat ttt aat gcg aaa atc gac ggc tta ggt gct act tca gcc act    624
Ala Tyr Phe Asn Ala Lys Ile Asp Gly Leu Gly Ala Thr Ser Ala Thr
        195                 200                 205 aga tac ggt gat aat cgt act aac tat aga ttc gat gtt gga cag gct    672
Arg Tyr Gly Asp Asn Arg Thr Asn Tyr Arg Phe Asp Val Gly Gln Ala
210                 215                 220 gta tac gcg cct gga aca tta ata tat gtg ttt gaa att ata gat ggt    720
Val Tyr Ala Pro Gly Thr Leu Ile Tyr Val Phe Glu Ile Ile Asp Gly
225                 230                 235                 240 tgg tgt cgc att tat tgg aac aat cat aat gag tgg ata tgg cat gag    768
Trp Cys Arg Ile Tyr Trp Asn Asn His Asn Glu Trp Ile Trp His Glu
                245                 250                 255 aga ttg att gtg aaa gaa gtg ttt ccc ggg ggg ggt tct cat cat cat    816
Arg Leu Ile Val Lys Glu Val Phe Pro Gly Gly Gly Ser His His His
            260                 265                 270 cat cat cat taa                                                    828
His His His
        275

<210> SEQ ID NO 6
<211> LENGTH: 275
<212> TYPE: PRT
<213> ORGANISM: Artificial Sequence
<220> FEATURE:
<223> OTHER INFORMATION: Synthetic Construct

<400> SEQUENCE: 6

Met Val Lys Leu Asn Asp Val Leu Ser Tyr Val Asn Gly Leu Val Gly
1               5                   10                  15

Lys Gly Val Asp Ala Asp Gly Trp Tyr Gly Thr Gln Cys Met Asp Leu
            20                  25                  30

Thr Val Asp Val Met Gln Arg Phe Phe Gly Trp Arg Pro Tyr Gly Asn
        35                  40                  45

Ala Ile Ala Leu Val Asp Gln Pro Ile Pro Ala Gly Phe Gln Arg Ile
    50                  55                  60

Arg Thr Thr Ser Ser Thr Gln Ile Lys Ala Gly Asp Val Met Ile Trp
65                  70                  75                  80
```

```
            Gly Leu Gly Tyr Tyr Ala Gln Tyr Gly His Thr Gly Ile Ala Thr Glu
                            85                  90                  95

Asp Gly Arg Ala Asp Gly Thr Phe Val Ser Val Asp Gln Asn Trp Ile
                        100                 105                 110

Asn Pro Ser Leu Glu Val Gly Ser Pro Ala Ala Ile His His Asn
                    115                 120                 125

Met Asp Gly Val Trp Gly Val Ile Arg Pro Pro Tyr Glu Ala Glu Ser
                130                 135                 140

Lys Pro Lys Pro Pro Ala Pro Lys Pro Asp Lys Pro Asn Leu Gly Gln
            145                 150                 155                 160

Lys Val Lys Pro Pro Ala Gln Lys Ala Val Gly Lys Ser Ala Ser Lys
                            165                 170                 175

Ile Thr Val Gly Ser Lys Ala Pro Tyr Asn Leu Lys Trp Ser Lys Gly
                        180                 185                 190

Ala Tyr Phe Asn Ala Lys Ile Asp Gly Leu Gly Ala Thr Ser Ala Thr
                        195                 200                 205

Arg Tyr Gly Asp Asn Arg Thr Asn Tyr Arg Phe Asp Val Gly Gln Ala
                        210                 215                 220

Val Tyr Ala Pro Gly Thr Leu Ile Tyr Val Phe Glu Ile Ile Asp Gly
            225                 230                 235                 240

Trp Cys Arg Ile Tyr Trp Asn Asn His Asn Glu Trp Ile Trp His Glu
                            245                 250                 255

Arg Leu Ile Val Lys Glu Val Phe Pro Gly Gly Gly Ser His His His
                        260                 265                 270

His His His
                    275
```